(12) United States Patent
Meiron et al.

(10) Patent No.: US 9,096,827 B2
(45) Date of Patent: Aug. 4, 2015

(54) ADHERENT CELLS FROM PLACENTA TISSUE AND USE THEREOF IN THERAPY

(75) Inventors: Moran Meiron, Zikhron-Yaakov (IL); Amir Toren, Zikhron-Yaakov (IL); Rachel Ofir, Mitzpe Adi (IL); Nirit Drori-Carmi, Doar-Na Hof HaCarmel (IL)

(73) Assignee: Pluristem Ltd., Haifa (IL)

( * ) Notice: Subject to any disclaimer, the term of this patent is extended or adjusted under 35 U.S.C. 154(b) by 203 days.

(21) Appl. No.: 13/061,656

(22) PCT Filed: Sep. 1, 2009

(86) PCT No.: PCT/IL2009/000845
§ 371 (c)(1),
(2), (4) Date: Jul. 8, 2011

(87) PCT Pub. No.: WO2010/026574
PCT Pub. Date: Mar. 11, 2010

(65) Prior Publication Data
US 2011/0256160 A1    Oct. 20, 2011

Related U.S. Application Data

(60) Provisional application No. 61/202,049, filed on Jan. 23, 2009, provisional application No. 61/136,377, filed on Sep. 2, 2008.

(51) Int. Cl.
| | |
|---|---|
| C12N 5/00 | (2006.01) |
| C12N 5/071 | (2010.01) |
| C12M 1/00 | (2006.01) |
| C12N 5/073 | (2010.01) |
| A01N 1/02 | (2006.01) |
| C12N 5/0775 | (2010.01) |
| A61K 35/50 | (2015.01) |
| A61K 35/12 | (2015.01) |

(52) U.S. Cl.
CPC ............... *C12N 5/0605* (2013.01); *A01N 1/02* (2013.01); *A61K 35/12* (2013.01); *A61K 35/50* (2013.01); *C12N 5/00* (2013.01); *C12N 5/0662* (2013.01); *C12N 5/0668* (2013.01)

(58) Field of Classification Search
CPC ...... C12N 5/00; C12N 5/0662; C12N 5/0668; A01N 1/02; A61K 35/50
USPC ............................. 435/289.1, 366, 374, 378
See application file for complete search history.

(56) References Cited

U.S. PATENT DOCUMENTS

| | | | |
|---|---|---|---|
| 2006/0171932 | A1* | 8/2006 | Hendricks et al. |
| 2007/0122393 | A1* | 5/2007 | McIntosh et al. |
| 2007/0190042 | A1* | 8/2007 | Edinger et al. |
| 2007/0275362 | A1* | 11/2007 | Edinger et al. |
| 2011/0129486 | A1* | 6/2011 | Merion |
| 2013/0259845 | A1* | 10/2013 | Heidaran et al. |

FOREIGN PATENT DOCUMENTS

WO    WO 2007/108003    *  9/2007

OTHER PUBLICATIONS

Li et al., 2005, Cell research, vol. 15, No. 7, p. 539-547.*
Fukuchi et al., 2004, Stem Cells, vol. 22, p. 649-658.*
Allegrucci et al., 2006, Human Reproduction Update, vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Xue et al., 2005, Suzhou Daxue Xuebao, Yixueban, vol. 25(2), abstract.*
Pilz et al., Human term placenta-derived mesenchymal stromal cells are less prone to osteogenic differentiation than bone marrow-derived mesenchymal stromal cells. Stem Cells Dev. Apr. 2011;20(4):635-46. doi: 10.1089/scd.2010.0308. Epub Jan. 27, 2011.
Portmann-Lanz et al., Placental mesenchymal stem cells as potential autologous graft for pre-and perinatal neuroregeneration. Am J Obstet Gynecol. Mar. 2006;194(3):664-73.

* cited by examiner

*Primary Examiner* — Shin Lin Chen
(74) *Attorney, Agent, or Firm* — Wolf, Greenfield & Sacks, P.C.

(57) ABSTRACT

A method of culturing adherent cells from a placenta or adipose tissue is disclosed. The method comprising culturing the adherent cells from the placenta or adipose tissue under 2 dimensional (2D) culturing conditions which allow cell expansion, the conditions comprising continuous passaging of the cells for at least 4 passages.

15 Claims, 6 Drawing Sheets

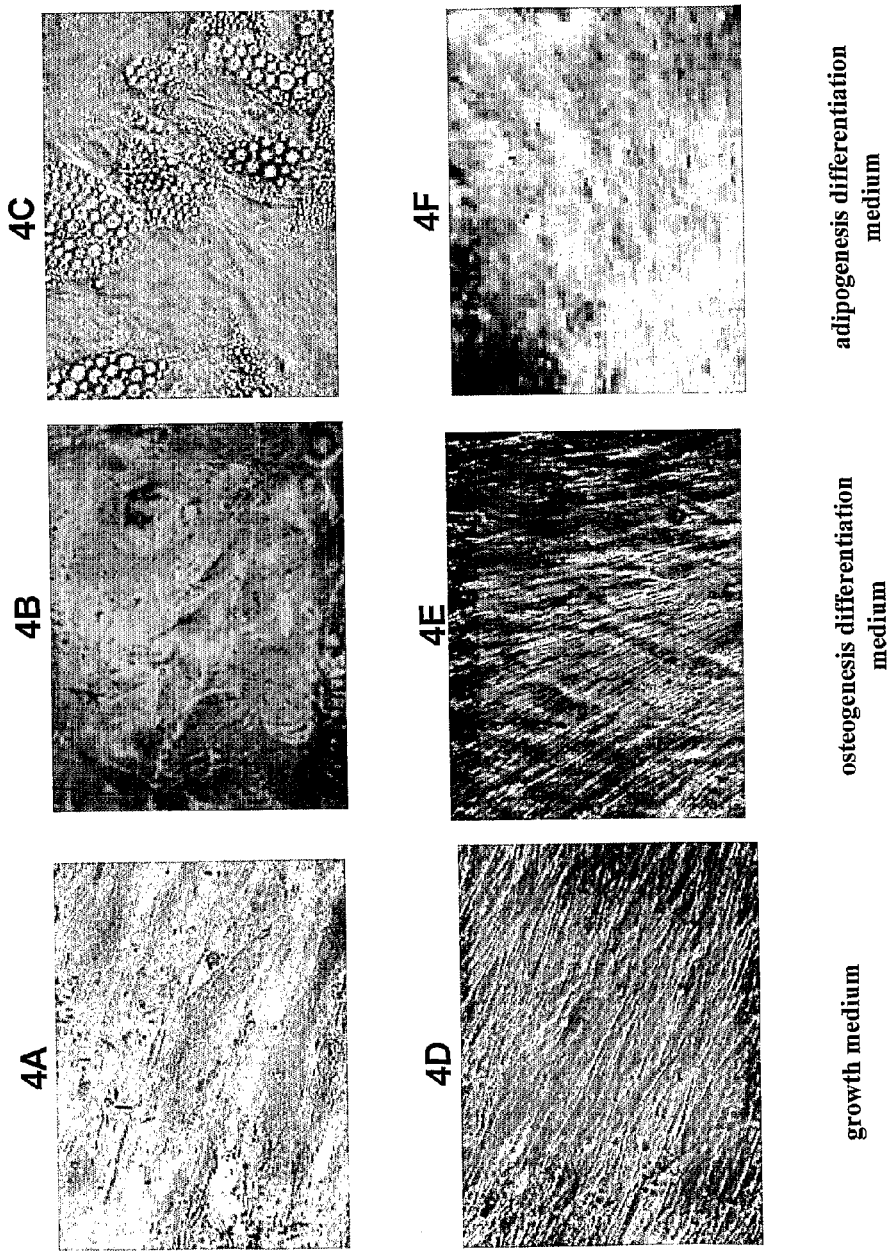
FIGs. 4A-F

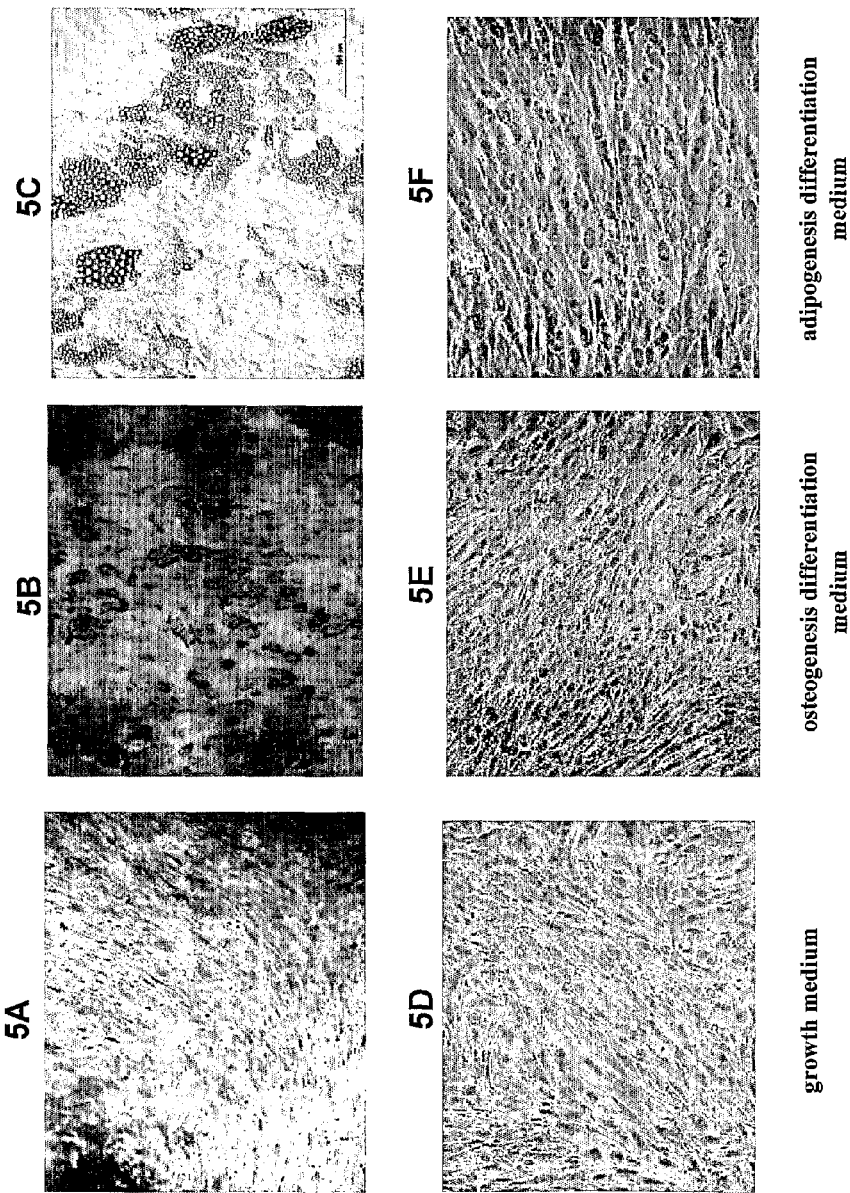
FIGs. 5A-F

US 9,096,827 B2

ADHERENT CELLS FROM PLACENTA TISSUE AND USE THEREOF IN THERAPY

This application is the National Phase of International Application Number PCT/IL2009/000845, filed Sep. 1, 2009, and claims the benefit of U.S. Provisional Patent Application No. 61/202,049, filed Jan. 23, 2009 and U.S. Provisional Patent Application No. 61/136,377, filed Sep. 2, 2008.

The contents of all of the above documents are incorporated by reference as if fully set forth herein.

FIELD AND BACKGROUND OF THE INVENTION

The present invention, in some embodiments thereof, relates to adherent cells of placenta tissue and, more particularly, but not exclusively; to methods of culturing same and using same for treatment.

In recent years, considerable activity has focused on the therapeutic potential of mesenchymal stromal cells (MSCs) for various medical applications including tissue repair of damaged organs such as the brain, heart, bone and liver and in support of bone marrow transplantations (BMT). MSCs, a heterogeneous population of cells obtained from e.g. bone marrow, adipose tissue, placenta, and blood, is capable of differentiating into different types of cells (e.g. reticular endothelial cells, fibroblasts, adipocytes, osteogenic precursor cells) depending upon influences from various bioactive factors. Accordingly, MSCs have been widely studied in regenerative medicine as the foundation to build new tissues such as bone, cartilage and fat for the repair of injury or replacement of pathologic tissues and as treatment for genetic and acquired diseases [Fibbe and Noort, Ann N Y Acad Sci (2003) 996: 235-44; Horwitz et al., Cytotherapy (2005) 7(5): 393-5; Zimmet and Hare, Basic Res Cardiol (2005) 100(6): 471-81]. Furthermore, the multipotent ability of MSCs, their easy isolation and culture, as well as their high ex vivo expansion potential make them an attractive therapeutic tool [Fibbe and Noort, supra; Minguell et al. Exp Biol Med (Maywood) (2001) 226(6): 507-20].

An emerging body of data indicates that MSCs escape recognition of alloreactive cells and are considered to be immune privileged [Le Blanc et al., Exp Hematol (2003) 31(10): 890-6]. Having low immunogenicity, MSCs are not rejected by the patient's immune system and therefore are considered not to require HLA matching.

Placental derived MSCs exhibit many markers common to MSCs isolated from other tissues, e.g. CD105, CD73, CD90 and CD29, and the lack of expression of hematopoietic, endothelial and trophoblastic-specific cell markers. Adipogenic, osteogenic, and neurogenic differentiation have been achieved after culturing placental derived MSCs under appropriate conditions [Yen et al., Stem Cells (2005) 23(1): 3-9]. Furthermore, MSCs isolated from placenta and cultured in vitro have been demonstrated to be immune privileged in a similar fashion as MSCs [Li et al., Cell Res (2005) 15(7): 539-47]. Thus, the placenta provides an ethically non-controversial and easily accessible source of MSCs for experimental and clinical applications [Zhang et al., Exp Hematol (2004) 32(7): 657-64]. In addition, the present inventors have previously devised three dimensional (3D) culturing conditions suitable for expansion of placental derived MSCs (WO/2007/108003).

SUMMARY OF THE INVENTION

According to an aspect of some embodiments of the present invention there is provided a method of culturing adherent cells from a placenta or adipose tissue, the method comprising culturing the adherent cells from the placenta or adipose tissue under 2 dimensional (2D) culturing conditions which allow cell expansion, the conditions comprising continuous passaging of the cells for at least 4 passages.

According to some embodiments of the invention, the method further comprises growing the cells in a culture medium devoid of an antibiotic from at least passage 2.

According to an aspect of some embodiments of the present invention there is provided a population of cells generated according to the above method.

According to an aspect of some embodiments of the present invention there is provided a population of cells comprising a gene expression profile essentially as described herein.

According to an aspect of some embodiments of the present invention there is provided a use of the population of cells, for the manufacture of a medicament identified for treating a condition which can benefit from cell or organ transplantation.

According to an aspect of some embodiments of the present invention there is provided a method of inducing tolerance and/or immunosuppression in a subject in need thereof, the method comprising administering to the subject a therapeutically effective amount of adherent cells, thereby inducing tolerance and/or immunosuppression in the subject.

According to some embodiments of the invention, at least 12% of the adherent cells are at a proliferative phase.

According to some embodiments of the invention, the adherent cells are capable of suppressing an immune reaction.

According to some embodiments of the invention, the adherent cells comprise a positive marker expression selected from the group consisting of CD73, CD90, CD29 and CD105.

According to some embodiments of the invention, the adherent cells comprise a negative marker expression selected from the group consisting of CD11b, CD34, HLA-DR, CD14, CD19, CD200 and CD45.

According to some embodiments of the invention, the adherent cells comprise a gene expression profile essentially as described herein.

According to some embodiments of the invention, the adherent cells are less committed to an osteogenic lineage as compared to adherent cells from bone marrow grown and allowed to differentiate under the same conditions.

According to some embodiments of the invention, the adherent cells are less committed to an adipogenic lineage as compared to adherent cells from bone marrow grown and allowed to differentiate under the same conditions.

According to some embodiments of the invention, the condition is selected from the group consisting of ischemia, peripheral arterial disease (PAD), critical limb ischemia (CLI), lower extremity, ischemia, ischemic vascular disease, vascular disease of the kidney, ischemic heart disease, myocardial ischemia, coronary artery disease (CAD), atherosclerotic cardiovascular disease, left main coronary artery disease, arterial occlusive disease, peripheral ischemia, peripheral vascular disease, arteriosclerosis, ischemic brain disease, stroke, cerebral ischemia, cerebro vascular disease, retinopathy, retinal repair, remodeling disorder, von Hippel-Lindau syndrome, hereditary hemorrhagic telengiectasiaischemic vascular disease, Buerger's disease, ischemic renal disease, ischemic placenta, reproduction associated disorders, graft-versus-host disease, solid organ transplantation, hematopoietic stem cell transplantation, diabetes, connective tissue damage, cancer, pre-cancer, bone cancer, osteosarcoma, bone metastases, bone fracture, burn wound, articular cartilage defect, deep wound, delayed wound-healing, delayed ulcer healing, subchondral-bone cyst, osteoporosis, osteoarthritis, degenerated bone, cartilage damage, articular cartilage defect, injured tendons, autoimmune diseases, metabolic disorders, psoriasis, neuropathic pain, peripheral nerve injury, support of kidney transplantation and inflammatory diseases.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-F are photographs depicting growth of bone marrow and placenta cells under osteogenesis or adipogenesis differentiation conditions. Bone marrow derived cells (FIGS. 4A-C) or placenta derived cells (FIGS. 4D-F) were plated in growth medium (FIGS. 4A and 4D), osteogenesis differentiation medium (FIGS. 4B and 4E) or adipogenesis differentiation medium (FIGS. 4C and 4F) in a 24 well plate coated with vitronectin and collagen. Medium was replaced every 3-4 days. At the end of growth period cells were fixed, stained and pictured as described in detail the Examples section which follows.

FIGS. 5A-F are photographs depicting growth of bone marrow and placenta cells under modified osteogenesis or adipogenesis differentiation conditions. Bone marrow derived cells (FIGS. 5A-C) or placenta derived cells (FIGS. 5D-F) were plated in growth medium (FIGS. 5A and 5D), osteogenesis differentiation medium (FIGS. 5B and 5E) or adipogenesis differentiation medium (FIGS. 5C and 5F) in a 24 well plate coated with vitronectin and collagen. Medium was replaced every 3-4 days. At the end of growth period cells were fixed, stained and pictured as described in detail the Examples section which follows.

DESCRIPTION OF SPECIFIC EMBODIMENTS OF THE INVENTION

Figure 1A:
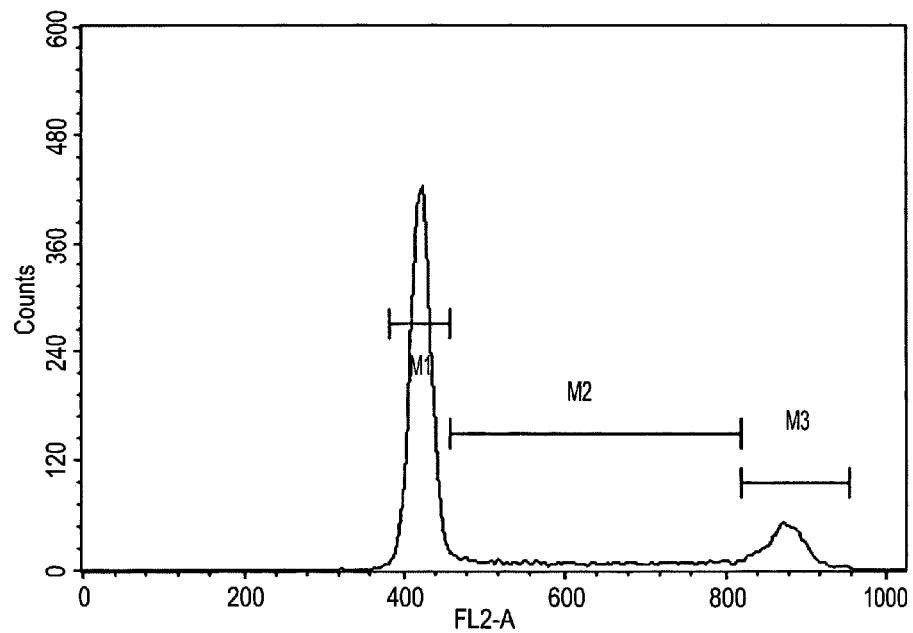
FIGS. 1A-B are figures depicting cell cycle analysis of adherent cells of placenta grown according to the present teachings (FIG. 1A) or adherent cells manufactured according to the teachings of WO/2007/108003, designated PLX (FIG. 1B). Cells were fixed in 70% EtOH O.N, centrifuged and re-suspended in a Propidium Iodide (PI) solution and then analyzed by FACS.

The present invention, in some embodiments thereof, relates to adherent cells of placenta tissue and, more particularly, but not exclusively, to methods of culturing same and using same for treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that placenta adherent cells cultured ex vivo under specific 2D conditions, are capable of suppressing an immune response and are highly proliferative and thus may be used for therapeutic applications.

As is illustrated herein below and in Example 1-3 of the Examples section which follows, the present inventors were able to expand placenta-derived adherent cells under specific 2D conditions. The 2D conditions of the present invention comprise continuous passaging of the cells for at least 4 passages and optionally include incubating the cells with antibiotic supplement only during the initial two passages of cell growth (see Example 2). Moreover, unlike the previously described methods (see Example 1 and WO/2007/108003) wherein the cells are cryopreserved during the growth process, the present teachings teach cryopreservation of the cells only at the end of culture (e.g., after 5-6 passages). As is shown in Example 3, the placenta derived 2D adherent cells of the present invention comprise stromal stem cells properties e.g. they express cellular markers typical of stromal stem cells and comprise immunosuppressive properties. Furthermore, these cells are highly proliferative (28% of cells were in S and G2/M phases) suggesting that the 2D culturing conditions are optimal to support cell growth.

In addition, the placenta derived 2D adherent cells of the present invention did not differentiation into osteocytes (Examples 4-5) or adipocytes (Examples 6-7), in sharp contrast to bone marrow adherent cells grown under the same conditions.

Thus, according to one aspect of the present invention there is provided a method of culturing adherent cells from a placenta or adipose tissue, the method comprising culturing the adherent cells from the placenta or adipose tissue under 2 dimensional (2D) culturing conditions which allow cell expansion, the conditions comprising continuous passaging of the cells for at least 4 passages.

As used herein the phrase "adherent cells" refers to a homogeneous or heterogeneous population of cells which are anchorage dependent, i.e., require attachment to a surface in order to grow in vitro.

As used herein the phrase "adipose tissue" refers to a connective tissue which comprises fat cells (adipocytes).

As used herein the term "placenta tissue" refers to any portion of the mammalian organ which lines the uterine wall and during pregnancy envelopes the fetus, to which it is attached by the umbilical cord. Following birth, the placenta is expelled (and is referred to as a post partum placenta). In an exemplary embodiment, placenta refers to whole placenta.

According to the present teachings, placenta or adipose tissue derived adherent cells are propagated using two dimensional (2D) culturing conditions.

As used herein the phrase "two dimensional culture" refers to a culture in which the cells are disposed to conditions which are compatible with cell growth while allowing the cells to grow in one plane. The conditions in the two dimensional culture of the invention are designed to enable expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such stationarity.

As mentioned, the adherent cells of this aspect of the invention are retrieved from a placental or adipose tissue.

Placental cells may be obtained from a full-term or preterm placenta. Placenta is preferably collected once it has been ex blooded. The placenta is preferably perfused for a period of time sufficient to remove residual cells (i.e., red blood cells). The term "perfuse" or "perfusion" used herein refers to the act of pouring or passaging a fluid over the placenta or in the later stages of the method over the cultured cells. The placental tissue may be from any mammal; for example, the placental tissue is human. A convenient source of placental tissue is from a post partum placenta (e.g., 1-6 hours), however, the source of placental tissue or cells or the method of isolation of placental tissue is not critical to the invention.

Placenta derived adherent cells may be obtained from both fetal (i.e., amnion, chorion, chorionic villi or inner parts of the placenta, see Example 1) and maternal (i.e., decidua basalis, and decidua parietalis) parts of the placenta. Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

It will be appreciated that adherent cells may be derived from adipose tissue. Adipose tissue derived adherent cells may be isolated by a variety of methods known to those skilled in the art. For example, such methods are described in U.S. Pat. No. 6,153,432. The adipose tissue may be derived from omental/visceral, mammary, gonadal, or other adipose tissue sites. One source of adipose tissue is omental adipose. In humans, the adipose is typically isolated by liposuction.

Isolated adherent cells from placenta or adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. Cells are centrifuged at speeds of between 100 to 3000×g for periods of between 1 minutes to 1 hour at temperatures of between 4-50° C. (see U.S. Pat. No. 7,078,230).

Cell retrieval from placenta or adipose tissue is preferably effected under aseptic conditions. Once isolated cells are obtained, they are allowed to adhere to an adherent material (e.g., configured as a surface) to thereby isolate adherent cells. Culturing then proceeds under 2D conditions (as described herein and in Example 2 of the Examples section which follows).

As used herein "an adherent material" refers to a synthetic, naturally occurring or a combination of same of a non-cyto-toxic (i.e., biologically compatible) material having a chemical structure (e.g., charged surface exposed groups) which may retain the cells on a surface.

Examples of adherent materials which may be used in accordance with this aspect of the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, vitronectin chondronectin, laminin), a dextran, a collagen, a poly L lactic acid and an inert metal fiber.

It will be appreciated that seeding of placenta or adipose cells is typically effected at a culture density of $3\pm0.2\times10^3$ cells/cm$^2$. Following seeding, cell cultures are usually cultured in a tissue culture incubator under humidified conditions with 5% CO2 at 37° C.

Further steps of purification or enrichment for stromal stem cells may be effected using methods which are well known in the art (such as by FACS using stromal stem cell marker expression, as further described herein below).

Non-limiting examples of base media useful in culturing according to the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of human, bovine or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells. Additionally, components may be added to enhance the differentiation process when needed (see further below).

According to an embodiment of the present invention, the cells are grown in a culture medium devoid of antibiotic supplements from at least passage 2, at least passage 3, or at least passage 4.

As mentioned, once adherent cells are at hand they may be continuously passaged. According to an embodiment of the present invention, the cells are passaged for at least 4 passages, at least 5 passages, at least 6 passages, at least 7 passages or at least 8 passages. It will be appreciated that cells are typically passaged when the culture reaches about 70-90% confluence, typically after 3-7 days (e.g., 3-5 days, 1-3 doublings).

Culturing is effected for at least about 2 days, 3 days, 4 days, 5 days, 6 days, 7 days, 10 days, 14 days, 20 days, a month or even more. Passaging may also be effected to increase cell number. It will be appreciated that culture medium may be changed in order to prolong and improve culturing conditions.

Cells can be harvested when at least about 10% of cells are proliferating while avoiding uncontrolled differentiation and senescence.

Adherent cells of some embodiments of the present invention comprise at least about 10%, 28%, 30%, 50%, 80% or more proliferative cells (as can be assayed by FACS monitoring S and G2/M phases).

Adherent cells of some embodiments of the invention may comprise at least one "stromal stem cell phenotype".

As used herein "a stromal stem cell phenotype" refers to a structural or functional phenotype typical of a bone-marrow derived stromal (i.e., mesenchymal) stem cell.

As used herein the phrase "stem cell" refers to a cell which is not terminally differentiated.

Thus for example, the cells may have a spindle shape. Alternatively or additionally the cells may express a marker or a collection of markers (e.g. surface marker) typical to stromal stem cells. Examples of stromal stem cell surface markers (positive and negative) include but are not limited to CD105+, CD29+, CD44+, CD73+, CD90+, CD3−, CD4−, CD34−, CD45−, CD80−, CD5−, CD20−, CD11B−, CD14−, CD19−, CD79−, HLA-DR−, and FMC7−. Other stromal stem cell markers include but are not limited to tyrosine hydroxylase, nestin and H—NF.

Adherent cells of placenta tissue generated according to the present teachings have a gene expression profile essentially as described in Example 3 of the Examples section which follows.

Examples of functional phenotypes typical of stromal stem cells include at least one of the following, but are not limited to, T cell suppression activity (they don't stimulate T cells and conversely suppress same) and hematopoietic stem cell support activity.

According to an exemplary embodiment, the adherent cells of the present invention are less committed to differentiation into osteogenic or adipogenic lineages as compared to adherent cells from the bone marrow grown and differentiated under the same conditions (see Examples 4-5 and Examples 6-7, respectively).

As is shown in Example 3 of the Examples section which follows, the adherent 2D cells of the present invention were found to suppress the immune reaction of human peripheral blood mononuclear cells, thus the cells exhibit biological activities which may be preferentially used in the clinic (e.g., T cell suppression activity, hematopoietic stem cell support activity).

According to one embodiment of the invention, the adherent cells of the invention are capable of suppressing an immune reaction in a subject.

As used herein the phrase "suppressing an immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively.

The populations of cells generated according to the present teachings may be used for treating a condition which can benefit from cell or organ transplantation.

As used herein, the term "condition" refers to any pathology (disease, condition, syndrome or disorder) which may benefit from cell (e.g. stem cell) or organ transplantation. Examples include ischemic conditions, cardiovascular conditions, nervous system conditions, gastrointestinal tract conditions, orthopedic conditions, hematopoietic conditions, renal conditions and hepatic conditions, such as but are not limited to, peripheral arterial disease (PAD), such as limb ischemia and critical limb ischemia (CLI), lower extremity ischemia, ischemic vascular disease, ischemic heart disease, myocardial ischemia, acute myocardial infarction (MI), coronary artery disease (CAD), atherosclerotic cardiovascular disease, left main coronary artery disease, arterial occlusive disease, peripheral ischemia, peripheral vascular disease, arteriosclerosis, ischemic brain disease, stroke, cerebral ischemia, cerebro vascular disease, retinopathy, retinal repair, remodeling disorder, von Hippel-Lindau syndrome, hereditary hemorrhagic telengiectasiaischemic vascular disease, Buerger's disease, diabetes, vascular disease of the kidney, ischemic renal disease, liver disease, ischemic placenta, reproduction associated disorders, graft-versus-host disease (GVHD), solid organ transplant, hematopoietic stem cell transplantation (HSCT), inflammatory conditions of the gastrointestinal (GI) tract, ulcerative colitis, delayed wound-healing, delayed ulcer healing, cancer (e.g. breast cancer), pre-cancer, conditions characterized by connective tissue damage such as bone cancer, osteosarcoma, bone metastases, bone fracture, degenerative disc disease, osteogenesis imperfecta (OI), burn, burn wound, articular cartilage defect, deep wound, delayed wound-healing, delayed ulcer healing, metabolic disorders, psoriasis, neuropathic pain, peripheral nerve injury, support of kidney transplantation, subchondral-bone cyst, osteoporosis, osteoarthritis (OA), degenerated bone, cartilage damage, articular cartilage defect, injured tendons (e.g., overstrain-induced injuries of tendons) and injured ligaments.

It will be appreciated that the adherent cells of the present invention are capable of inducing immunosuppression and/or tolerance in a subject. Thus, the adherent cells may be used to treat any condition in need of immunosuppression and/or tolerance. Such conditions included, but are not limited to, autoimmune diseases and inflammatory diseases (including acute and chronic inflammatory diseases) including, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (492) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Furthermore, the adherent cells may be used to treat diseases associated with transplantation of a graft including, but are not limited to, graft rejection, chronic graft rejection, subacute graft rejection, hyperacute graft rejection, acute graft rejection and graft versus host disease.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" may also refer to alleviating or diminishing a symptom associated with the pathology.

The subject treated by the adherent cells may be any subject (e.g., a mammal), such as a human subject or a domesticated animal including, but not limited to, horses (i.e. equine), cattle, goat, sheep, pig, dog, cat, camel, alpaca, llama and yak who is diagnosed with or suffers from the pathology and can benefit from stem cell transplantation.

Methods of deriving lineage specific cells from the adherent cells (e.g. stromal stem cells) of the invention are well known in the art. See for example, U.S. Pat. Nos. 5,486,359, 5,942,225, 5,736,396, 5,908,784 and 5,902,741.

The adherent cells may be naïve or may be genetically modified such as to derive a lineage of interest (see U.S. Pat. Appl. No. 20030219423).

The cells may be of autologous or non-autologous source (i.e., allogeneic or xenogeneic) of fresh or frozen (e.g., i-preserved) preparations.

Depending on the medical condition, the subject may be administered with additional chemical drugs (e.g., immunomodulatory, chemotherapy etc.) or cells.

Even though the cells are characterized by immuno-suppressive activity, they may still provoke host or donor-derived undesirable immune response. Approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise micro architectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Furthermore, it will be appreciated that the cells can be administered either per se or, preferably as a part of a pharmaceutical composition that further comprises a pharmaceutically acceptable carrier.

As used herein a "pharmaceutical composition" refers to a preparation of the adherent cells of the invention (i.e., adherent cells), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in vitro, in cell cultures or experimental animals.

Depending on the severity and responsiveness of the condition to be treated, dosing can be of a single or a plurality of administrations. However, the amount of a composition to be administered will, of course, be dependent on the subject being treated, the severity of the affliction, the manner of administration, the judgment of the prescribing physician, etc.

Following transplantation, a portion of the cells of the invention preferably survive in the diseased area for a period of time (e.g. about 2-6 weeks), such that a therapeutic effect is observed.

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533;

3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Production of Placenta Derived 3D Adherent Cells

Adherent cells were produced as was previously described (see WO/2007/108003) in a bioreactor system containing 3D carriers to produce 3D-adherent cells (designated herein as PLX).

Materials and Experimental Procedures

Placenta Derived Adherent Cells—

Inner parts of a full-term delivery placenta (Bnei Zion medical center, Haifa, Israel) were cut under aseptic conditions, washed 3 times with Hank's Buffer and incubated for 3 hours at 37° C. with 0.1% Collagenase (1 mg/ml tissue; Sigma-Aldrich, St. Lewis, Mo.). Using gentle pipetting, suspended cells were then washed with DMEM supplemented with 10% FCS, Pen-Strep-Nystatin mixture (100 U/ml:100 µg/ml:1.25 un/ml) and 2 mM L-glutamine, seeded in 75 cm² flasks and incubated at 37° C. in a tissue culture incubator under humidified condition with 5% $CO_2$.

Two Dimensional (2D) Cell Growth

Cells were allowed to adhere to a plastic surface for 48-72 hours after which the media was changed every 3-4 days. After 2-3 passages, the cells were cryopreserved, thawed and seeded for a secondary growth in flasks. When reaching 60-80% confluence cells were detached from the growth flask using 0.25% trypsin-EDTA and seeded into new flasks (usually every 3-5 days), for another 2-5 passages. Cultured cells were thereafter collected for analysis or for culturing in bioreactors.

PluriX™ Plug Flow Bioreactor—

The PluriX™ Plug Flow bioreactor (Pluristem, Haifa, Israel; see U.S. Pat. No. 6,911,201 and WO/2007/108003), was loaded with 1-100 ml packed 3D porrosive carriers (4 mm in diameter) made of a non woven fabric matrix of polyester. These carriers enable the propagation of large cell numbers in a relatively small volume. Glassware was designed and manufactured by Pluristem (Pluristem, Haifa, Israel). The bioreactor was maintained in an incubator of 37° C., with flow rate regulated and monitored by a valve, and peristaltic pump. The bioreactor contains a sampling and injection point, allowing the sequential seeding of cells. Culture medium was supplied at pH 6.7-7.4 from a reservoir. The reservoir was supplied by a filtered gas mixture, containing air/$CO_2$/$O_2$ at differing proportions, depending on cell density in the bioreactor. The $O_2$ proportion was suited to the level of dissolved $O_2$ at the bioreactor exit, determined by a monitor. The gas mixture was supplied to the reservoir via silicone tubes or diffuser (Degania Bet, Emek Hayarden, Israel). The culture medium was passed through a separating container which enables collection of circulating, nonadherent cells. Circulation of the medium was obtained by a peristaltic pump. The bioreactor was further equipped with an additional sampling point and containers for continuous medium exchange.

Production of 3D-Adherent Cells (PLX)—

Non-confluent primary human adherent 2D cell cultures, grown as described above, were trypsinized, washed, resuspended in DMEM supplemented with 10% FBS, Pen-Strep-Nystatin mixture (100 U/ml:100 ug/ml:1.25 un/ml) and 2 mM L-glutamine, and seeded ($10^3$-$10^5$ cells/ml) via an injection point onto the 3D carriers in an aseptic Plug Flow bioreactor. Prior to inoculation, bioreactor was filled with PBS-Ca—Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow was kept at a rate of 0.1-5 ml/min. Seeding process involved cease of circulation for 2-48 hrs, thereby allowing the cells to settle on the carriers. Bioreactor was kept under controlled temperature (37° C.) and pH conditions (pH=6.7-7.4); using an incubator supplied with sterile air and $CO_2$ as needed. Growth medium was replaced 2-3 times a week. Circulation medium was replaced with fresh DMEM media, every 4 hr to 7 days. At a density of $1\times10^6$-$1\times10^7$ cells/ml (following 12-40 days of growth), total medium volume was removed from the bioreactor and bioreactor and carriers were washed 3-5 times with PBS. 3D-adherent cells were then detached from the carriers with Trypsin-EDTA; (Biological Industries, Beit Ha'emek, Israel; 3-15 minutes with gentle agitation, 1-5 times), and were thereafter resuspended in DMEM and cryopreserved.

Example 2

Production of the Placenta Derived 2D Adherent Cells of the Present Invention 2D adherent cells were produced which exhibit different characteristics then the above described 3D adherent cells.

Materials and Experimental Methods

Manufacturing Process of 2D Adherent Cells

Receipt of Human Tissue

All placentas obtained were received from the maternity ward under approval of the Helsinki Committee of the medical facility. Accordingly, all placenta donors signed an informed consent and Donor Screening and Donor Testing was performed (IPC1). Immediately after taking the placenta from the donor (during the caesarean procedure), it was placed in an aseptic plastic bag and then in a temperature-preserving box with ice packs Recovery and Processing of Adherent Cells To initiate the process, the placenta was cut into pieces under aseptic conditions under laminar flow hood, washed with Hank's buffer solution and incubated for 2-5 hours at 37° C. with 0.1% Collagenase (1 mg Collagenase/ml tissue). 2D cell medium (2D-Medium comprising DMEM supplemented with 10% FBS, fungizone 0.25 µg/ml and Gentamycine 50 µg/ml was added and the digested tissue was roughly filtered through a sterile metal strainer, collected in a sterile beaker and centrifuged (10 minutes, 1200 RPM, 4° C.). Using gentle pipeting, suspended cells were then diluted with 2D-Medium supplemented with antibiotics, seeded in 175 cm² flasks and incubated at 37° C. in a tissue culture incubator under humidified condition supplemented with 5% $CO_2$. Following 2-3 days, in which the cells were allowed to adhere to the flask surface, they were washed with PBS and 2D-Medium was added.

Two Dimensional (2D) Cell Growth

Prior to the first passage, growth medium samples of 10% of the total flask number in quarantine was pooled and taken for mycoplasma testing (IPC2). If cells were found to be negative for Mycoplasma (EZ-PCR Mycoplasma kit, Biological Industries, Israel), cells were released from quarantine. After 1-2 additional passages, using 2D-Medium supplemented with antibiotics cells were transferred to the 2D production clean room (2DP). Once in Room 2DP, culture was continued for another 3-6 passages using 2D-Medium without antibiotics Throughout the process, cultures were grown in a tissue culture incubator under humidified conditions with 5% CO2 at 37° C. After a total of 6-9 passages (9-17 cell doublings), cells were collected and cryopreserved as the 2D-Cell Stock (2DCS).

The first passage was usually carried out after 7-15 days. Beginning at passage 2 and continuing until passage 6-8, cells were passaged when the culture reached 70-90% confluence, usually after 4-5 days (1.5-2 doublings). The cells were detached from the flasks using 0.25% trypsin-EDTA (4 minutes at 37° C.) and seeded in a culture density of $4\pm0.5\times10^3$ cells/cm$^2$. The size of the tissue culture flasks raised as the passages proceed. The culturing process started in 175 cm$^2$ tissue culture flask, continued in 500 cm$^2$ (Triple flask) and finally the cells were seeded into Cell Factory 10 tray (6320 cm$^2$).

Prior to cryopreservation, at the end of 2DCS growth period, the growth medium was collected and the sample was prepared to be sent to an approved GLP laboratory for Mycoplasma test (IPC 4).

Cryopreservation Procedure for 2D-Cell-Stock Product

For 2DCS cryopreservation, 2D-cultured cells were collected under aseptic conditions using 0.25% trypsin-EDTA. The cells were centrifuged (1200 RPM, 10', 4° C.), counted and re-suspended in 2D-Medium.

For freezing, cell suspensions were diluted 1:1 with 2D-Freezing Mixture (final concentrations was 10% DMSO, 40% FBS and 50% 2D-Medium). Approximately 1.5-2.5× 10$^9$ cells were manufactured from one placenta. 4 ml of the cells were stored at a final concentration of $10\times10^6$/ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer. This material was referred to as the 2D-Cell Stock (2DCS) batch.

Example 3

Comparison of the 3D Adherent Cells (PLX) to the 2D Adherent Cells of the Present Invention 3D adherent cells (PLX) produced as described hereinabove were compared to the new 2D adherent cells of the present invention.

Materials and Experimental Methods

Cell Cycle Analysis—

2D adherent cells and PLX cells were fixed with 70% EtOH O.N, centrifuged and re-suspended in a Propidium Iodide (PI) solution containing 2 µg/ml PI (Sigma), 0.2 mg/ml Rnase A (Sigma) and 0.1% (v/v) Triton (Sigma) for 30 minutes. Cell cycle was analyzed by FACS.

Gene Expression Array (Microarray)—

Adherent cells were obtained from human full term placentas and were expanded by 2D cultures or according to the teachings of WO/2007/108003 (as described in detail in Examples 1-2). Three different batches of cells were obtained from each of the expansion methods for further examination.

RNA was extracted from the cells (Qiagen-Rneasy micro kit) and applied to an Affymetrix whole genome expression array GeneChip® Human Exon 1.0 ST Array (Affymetrix, Santa Clara, Calif., USA).

FACS Analysis of Membrane Markers— cells were stained with monoclonal antibodies as previously described. In short, 400,000-600,000 cells were suspended in 0.1 ml flow cytometer buffer in a 5 ml test tube and incubated for 15 minutes at room temperature (RT), in the dark, with each of the following monoclonal antibodies (MAbs): FITC-conjugated anti-human CD29 MAb (eBioscience), PE conjugated anti human CD73 MAb (Becton Dickinson), PE conjugated anti human CD105 MAb (eBioscience), PE conjugated anti human CD90 MAb (Becton Dickinson), FITC-conjugated anti-human CD45 MAb (IQProducts), PE-conjugated anti-human CD19 MAb (IQProducts), PE conjugated anti human CD14 MAb (IQProducts), FITC conjugated anti human HLA-DR MAb (IQProduct), PE conjugated anti human CD34 MAb (IQProducts), FITC conjugated anti human CD31 MAb (eBioscience), FITC conjugated anti human IDR MAb (R&D systems), anti human fibroblasts marker (D7-FIB) MAb (ACRIS), FITC-conjugated anti-human CD80 MAb (BD), FITC-conjugated anti-human CD86 MAb (BD), PE conjugated anti-human CD200 MAb (BD), FITC-conjugated anti-human CD40 MAb (BD), FITC-conjugated anti-human HLA-ABC MAb (BD), Isotype IgG1 FITC conjugated (IQ Products), Isotype IgG1 PE conjugated (IQ Products).

Cells were washed twice with flow cytometer buffer, resuspended in 500 µl flow cytometer buffer and analyzed by flow cytometry using FC-500 Flow Cytometer (Beckman Coulter). Negative controls were prepared with relevant isotype fluorescence molecules.

Immunomodulation Assay

Human derived mononuclear cells (MNCs) were isolated from peripheral blood. Suspension of 200,000 MNCs per 200 µl medium (RPMI 1640 medium containing 20% FBS per 96 well) were stimulated with 10 µg PHA/ml (SIGMA) in the presence of 20,000 2D adherent cells for 5 days under humidified 5% $CO_2$ at 37° C. Four different batches of 2D adherent cells were used. Three replicates of each group were seeded in 96-well plated. During the last 18 hrs of the 5-day culture, cells were pulsed with 1 µC $^3$H-thymidine and further harvested over fiberglass filter. Thymidine uptake was quantified by a scintillation counter.

Experimental Results

As is illustrated in Table 1, below, processing of the 2D adherent cells of the present invention differed from the 2D stage of PLX (WO/2007/108003) in a few aspects. First, the new 2D adherent cell's culture medium is supplemented with antibiotics only during the initial culturing stage (up to passage 2). Also, the new 2D adherent cells are cryopreserved only after 5-8 passages (i.e. at the end of culture) and not, as in the PLX process, during intermediate stages of 2D growth.

TABLE 1

Comparison of the 2D adherent cells of the present invention to those produced for PLX in WO/2007/108003

| Parameter | WO/2007/108003 | 2D adherent cells of the present invention |
|---|---|---|
| Tissue culture flask | 80 $cm^2$ and 175 $cm^2$ | 175 $cm^2$, triple flasks and Multi Tray |
| Medium supplemented with antibiotics | In all stages of the process | Up to passage 2 (included) |
| Cryopreservation of 2DCS | After 2-3 passages, then cryopreserved, thawed and seeded for a secondary growth in flasks for 2-5 passages, prior to seeding in bioreactor | After 5-8 passages, then cryopreserved and thawed prior to use |
| Freezing container | 2 ml cryogenic vials | 5 ml cryogenic vials |
| Freezing volume | 1-1.5 ml | 4 ml |
| Freezing method | Freezing container (contains isopropyl alcohol) | Controlled rate freezer |

Changes in the manufacturing process of the new 2D adherent cells resulted in changes in characteristics of the obtained cells. These differences are summarized hereinbelow.

Cell Cycle Analysis of 2D Adherent Cells Compared to 3D Adherent Cells of WO/2007/108003—

2D adherent cells were compared to 3D adherent cells in order to examine the distribution of the cells between the different phases of the cell cycle. As is clear from FIGS. 1A-B, 2D adherent cells exhibited typical proliferating profile (distribution of cells between the different phases of cell cycle). Specifically, 28% of cells were in S and G2/M phases (FIG. 1A). These results indicated that cells were harvested during proliferation and that the culturing conditions supported cell growth.

Figure 1B:
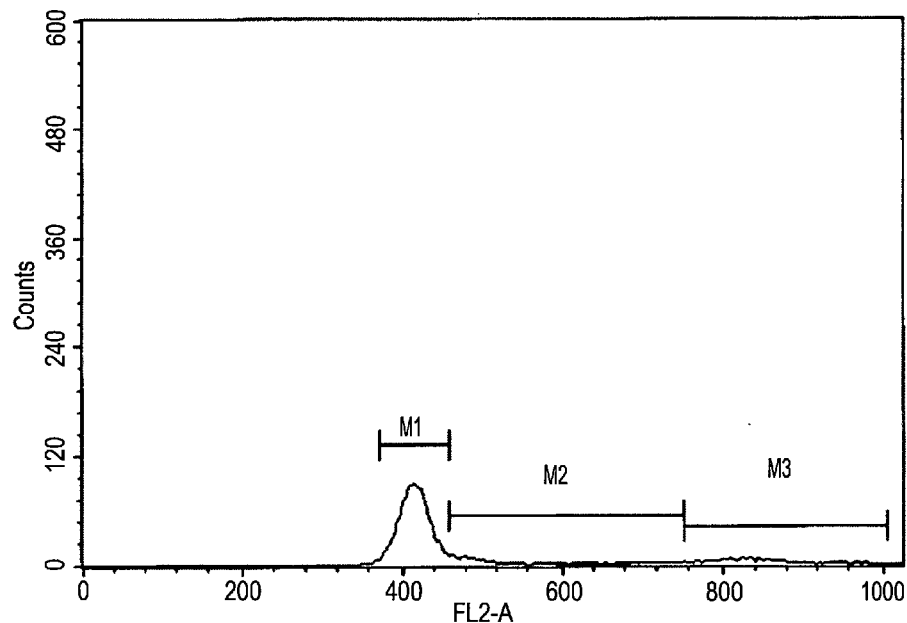

Conversely, 3D adherent cells exhibited lower rates of proliferating cells. Less than 8% of cells were in S and G2/M phases (FIG. 1B). These results indicated that cells were harvested while low levels of proliferation were taking place and suggest that conditions in the bioreactor were suboptimal to support cell growth.

Microarray Comparison Between Cells Obtained by the Teachings of WO/2007/108003 and by Cells Obtained by the Teachings of the Present Invention— gene expression arrays enabled to simultaneously monitor genome-wide expression profiles of adherent cells derived from human full term placentas expanded by 2D cultures or according to the teachings of WO/2007/108003 (PLX, see Example 1, hereinabove). These results enabled to asses the molecular mechanism underlying phenotypic variation between cells obtained by these different growth methods (see Table 2, below).

TABLE 2

Gene expression in 2D adherent cells of the present invention compared to those expressed by PLX of WO/2007/108003

| Gene | 2D vs. Plurix (fold change) | p-value (treat) |
|---|---|---|
| interferon-induced protein with tetratricopeptide repeats | 21.82 | 0.0401812 |
| leukocyte-derived arginine aminopeptidase | 14.56 | 3.88E−06 |
| signal peptide, CUB domain, EGF-like 3 | 10.82 | 0.0255115 |
| dickkopf homolog 1 (*Xenopus laevis*) | 6.84 | 3.06E−07 |
| integrin, alpha 6 | 6.76 | 0.0411667 |
| keratin 27 pseudogene 27 | 6.39 | 0.000224998 |
| similar to Keratin, type I cytoskeletal 18 (Cytokerati | 6.24 | 0.000304949 |
| aldehyde dehydrogenase 1 family, member A1 | 5.84 | 0.00145807 |
| G protein-coupled receptor, family C, group 5, member A | 5.75 | 3.39E−05 |
| coagulation factor III (thromboplastin, tissue factor) | 5.55 | 0.012192 |
| cyclin-dependent kinase inhibitor 3 (CDK2-associated dual | 5.51 | 0.000732492 |
| G protein-coupled receptor 126 | 5.50 | 0.00197635 |
| DEP domain containing 1 | 5.41 | 0.000370513 |
| SHC SH2-domain binding protein 1 | 4.96 | 0.00430878 |
| centrosomal protein 55 kDa | 4.78 | 0.0021952 |
| interferon-induced protein with tetratricopeptide repeats | 4.66 | 0.0139777 |
| NUF2, NDC80 kinetochore complex component, homolog (S. cere | 4.61 | 0.00276524 |
| mal, T-cell differentiation protein-like | 4.44 | 0.00664216 |
| interferon-induced protein with tetratricopeptide repea | 4.42 | 0.00357376 |
| kinesin family member 18A | 4.33 | 0.00134108 |
| cholinergic receptor, muscarinic 2 | 4.07 | 0.0320078 |
| cell division cycle 2, G1 to S and G2 to M | 4.06 | 0.0017111 |
| non-SMC condensin I complex, subunit G | 4.06 | 0.00537097 |
| denticleless homolog (*Drosophila*) | 4.06 | 0.00141153 |
| shugoshin-like 1 (*S. pombe*) | 4.00 | 0.00101318 |
| chromosome 13 open reading frame 3 | 3.98 | 0.000548296 |
| PDZ binding kinase | 3.97 | 0.00784983 |
| lymphocyte cytosolic protein 1 (L-plastin) | 3.97 | 0.0049584 |
| WAS | 3.96 | 0.00178153 |
| cyclin E2 | 3.94 | 0.000203389 |
| cathepsin C | 3.93 | 0.00532262 |
| integrin, alpha 4 (antigen CD49D, alpha 4 subunit of VLA-4 | 3.91 | 0.0158411 |
| KIAA0101 | 3.90 | 0.0105909 |
| kinesin family member 20A | 3.90 | 0.00582352 |
| opioid growth factor receptor-like 1 | 3.87 | 0.00114551 |
| anillin, actin binding protein | 3.83 | 0.010923 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| catenin (cadherin-associated protein), alpha-like 1 | 3.76 | 7.46E−05 |
| cell division cycle 20 homolog (*S. cerevisiae*) | 3.70 | 0.00514206 |
| diaphanous homolog 3 (*Drosophila*) | 3.69 | 0.00107709 |
| family with sequence similarity 111, member B | 3.69 | 0.000125819 |
| aurora kinase A | 3.66 | 0.00632571 |
| fibroblast growth factor 7 (keratinocyte growth factor) | 3.64 | 0.0328983 |
| maternal embryonic leucine zipper kinase | 3.63 | 0.00908391 |
| Rho GDP dissociation inhibitor (GDI) beta | 3.63 | 0.00200066 |
| centromere protein N | 3.62 | 0.000540143 |
| MAD2 mitotic arrest deficient-like 1 (yeast) | 3.62 | 0.00488102 |
| thymidylate synthetase | 3.61 | 0.00685584 |
| cyclin B2 | 3.60 | 0.016544 |
| regulator of G-protein signalling 4 | 3.59 | 0.00781061 |
| chromosome 6 open reading frame 173 | 3.58 | 0.00222408 |
| hyaluronan-mediated motility receptor (RHAMM) | 3.55 | 0.00467816 |
| BUB1 budding uninhibited by benzimidazoles 1 homolog (yeast | 3.54 | 0.0108258 |
| SPC25, NDC80 kinetochore complex component, homolog (S. ce | 3.53 | 0.00568662 |
| establishment of cohesion 1 homolog 2 (*S. cerevisiae*) | 3.52 | 0.000773033 |
| cyclin A2 | 3.51 | 0.00965934 |
| CDC28 protein kinase regulatory subunit 2 | 3.51 | 0.0128024 |
| keratin 18 | 3.47 | 0.000514523 |
| ribonucleotide reductase M2 polypeptide | 3.46 | 0.00834059 |
| arylacetamide deacetylase-like 1 | 3.44 | 0.000902645 |
| kinesin family member 11 | 3.43 | 0.00915145 |
| Rho GTPase activating protein 11A | 3.41 | 0.00834174 |
| GINS complex subunit 1 (Psf1 homolog) | 3.39 | 0.00104515 |
| discs, large homolog 7 (*Drosophila*) | 3.38 | 0.0317074 |
| TTK protein kinase | 3.38 | 0.0112171 |
| deleted in lymphocytic leukemia, 2 | 3.38 | 0.0109528 |
| replication factor C (activator 1) 3, 38 kDa | 3.37 | 0.00109668 |
| solute carrier family 7, (cationic amino acid transporte | 3.36 | 0.00688017 |
| dual-specificity tyrosine-(Y)-phosphorylation regulated ki | 3.34 | 0.0234606 |
| kinesin family member 2C | 3.34 | 0.0059888 |
| heat shock 22 kDa protein 8 | 3.32 | 0.0219583 |
| polo-like kinase 1 (*Drosophila*) | 3.30 | 0.0140309 |
| v-myb myeloblastosis viral oncogene homolog (avian)-lik | 3.28 | 0.0043878 |
| trypsinogen C | 3.28 | 0.00416276 |
| thymidine kinase 1, soluble | 3.27 | 0.00124134 |
| NAD(P)H dehydrogenase, quinone 1 | 3.27 | 0.000282423 |
| high-mobility group box 2 | 3.24 | 0.0196872 |
| cell division cycle associated 2 | 3.24 | 0.0122226 |
| apolipoprotein B mRNA editing enzyme, catalytic polypep | 3.23 | 0.00308692 |
| serpin peptidase inhibitor, clade B (ovalbumin), member | 3.22 | 0.0190218 |
| guanine nucleotide binding protein (G protein), gamma 11 | 3.22 | 0.00140559 |
| chromosome 15 open reading frame 23 | 3.21 | 0.000147331 |
| kinesin family member 14 | 3.19 | 0.00947901 |
| transmembrane protein 154 | 3.18 | 0.0045589 |
| glycerol kinase | 3.16 | 2.66E−05 |
| KIAA1524 | 3.15 | 0.0380688 |
| coagulation factor XIII, B polypeptide | 3.14 | 0.0294465 |
| tight junction protein 2 (zona occludens 2) | 3.13 | 0.00012562 |
| nei endonuclease VIII-like 3 (*E. coli*) | 3.12 | 0.00115606 |
| pleckstrin 2 | 3.11 | 0.0304429 |
| kinesin family member 23 | 3.09 | 0.00790585 |
| Rac GTPase activating protein 1 | 3.09 | 0.00381613 |
| keratinocyte growth factor-like protein 1 | 3.07 | 0.0300588 |
| keratinocyte growth factor-like protein 1 | 3.07 | 0.0300588 |
| keratinocyte growth factor-like protein 1 | 3.07 | 0.0300588 |
| transcription factor 19 (SC1) | 3.07 | 0.00109627 |
| OCIA domain containing 2 | 3.07 | 0.00122147 |
| lung cancer metastasis-associated protein | 3.06 | 0.00148024 |
| transcription factor 19 (SC1) | 3.05 | 0.00124327 |
| transcription factor 19 (SC1) | 3.05 | 0.00124327 |
| Rho GTPase activating protein 29 | 3.05 | 0.0466211 |
| glucosaminyl (N-acetyl) transferase 1, core 2 (beta-1,6-N- | 3.05 | 0.0197148 |
| replication factor C (activator 1) 4, 37 kDa | 3.04 | 0.00164152 |
| protein regulator of cytokinesis 1 | 3.01 | 0.0325664 |
| transforming, acidic coiled-coil containing protein 3 | 2.98 | 0.0014577 |
| cancer susceptibility candidate 5 | 2.96 | 0.0330594 |
| nucleolar and spindle associated protein 1 | 2.96 | 0.00520875 |
| cyclin B1 | 2.96 | 0.0103092 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| transmembrane protein 48 | 2.96 | 0.00458248 |
| ZW10 interactor | 2.95 | 1.88E−05 |
| endonuclease domain containing 1 | 2.95 | 0.000429245 |
| hypoxanthine phosphoribosyltransferase 1 (Lesch-Nyhan synd | 2.94 | 0.000634057 |
| fucosidase, alpha-L-2, plasma | 2.94 | 0.00540929 |
| ubiquitin-conjugating enzyme E2T (putative) | 2.93 | 0.00741886 |
| lipase A, lysosomal acid, cholesterol esterase (Wolman dise | 2.92 | 0.0167385 |
| villin 2 (ezrin) | 2.92 | 0.0131934 |
| glycerol kinase | 2.90 | 3.37E−06 |
| WD repeat domain 76 | 2.89 | 0.0023531 |
| CD97 molecule | 2.89 | 0.00994045 |
| chromosome 18 open reading frame 24 | 2.89 | 0.00347442 |
| topoisomerase (DNA) II alpha 170 kDa | 2.89 | 0.0321109 |
| integrin, alpha 3 (antigen CD49C, alpha 3 subunit of VLA-3 | 2.87 | 0.00574148 |
| family with sequence similarity 29, member A | 2.85 | 0.00111165 |
| kinesin family member 4A | 2.85 | 0.0114203 |
| BRCA1 associated RING domain 1 | 2.85 | 0.000540414 |
| serum | 2.84 | 0.0387246 |
| RAD51 homolog (RecA homolog, E. coli) (S. cerevisiae) | 2.83 | 0.000854739 |
| Fanconi anemia, complementation group I | 2.83 | 0.00464532 |
| dihydrofolate reductase | 2.82 | 0.00178879 |
| claspin homolog (Xenopus laevis) | 2.81 | 0.00683624 |
| ornithine decarboxylase 1 | 2.81 | 0.00144868 |
| sperm associated antigen 5 | 2.80 | 0.00906321 |
| histone cluster 1, H3b | 2.80 | 0.0304598 |
| ATPase family, AAA domain containing 2 | 2.79 | 0.00415258 |
| KIAA0286 protein | 2.79 | 0.00130563 |
| guanine nucleotide binding protein (G protein), alpha inhi | 2.76 | 0.00184597 |
| BUB1 budding uninhibited by benzimidazoles 1 homolog beta | 2.74 | 0.0166047 |
| dihydrofolate reductase pseudogene | 2.74 | 0.00141306 |
| brix domain containing 1 | 2.73 | 0.00471977 |
| cytoskeleton associated protein 2 | 2.72 | 0.0030499 |
| mitochondrial ribosomal protein S28 | 2.72 | 0.00298194 |
| polymerase (DNA directed), epsilon 2 (p59 subunit) | 2.72 | 0.00479612 |
| family with sequence similarity 72, member A | 2.72 | 0.00143248 |
| EBNA1 binding protein 2 | 2.70 | 0.00296292 |
| similar to 40S ribosomal protein SA (P40) (34 | 2.70 | 0.0385298 |
| adipose differentiation-related protein | 2.70 | 0.000331751 |
| thioredoxin reductase 1 | 2.70 | 0.000197486 |
| minichromosome maintenance complex component 5 | 2.69 | 0.00475504 |
| von Hippel-Lindau binding protein 1 | 2.69 | 0.00329061 |
| SCL | 2.68 | 0.00390288 |
| Fanconi anemia, complementation group D2 | 2.68 | 0.0281405 |
| NIMA (never in mitosis gene a)-related kinase 2 | 2.68 | 0.00289469 |
| PHD finger protein 19 | 2.68 | 0.000177604 |
| microsomal glutathione S-transferase 1 | 2.68 | 0.041701 |
| breast cancer 2, early onset | 2.68 | 0.00586847 |
| non-SMC condensin I complex, subunit H | 2.67 | 0.0216752 |
| chromosome 13 open reading frame 27 | 2.67 | 0.0234588 |
| histone cluster 1, H2bg | 2.67 | 0.000180822 |
| non-SMC condensin II complex, subunit G2 | 2.66 | 0.0130322 |
| centromere protein I | 2.64 | 0.0106816 |
| stomatin | 2.64 | 0.00387095 |
| glutathione S-transferase omega 1 | 2.63 | 0.000648379 |
| protein tyrosine phosphatase-like A domain containing | 2.62 | 0.0419644 |
| calcyclin binding protein | 2.62 | 0.00524566 |
| KIT ligand | 2.61 | 0.00641955 |
| ubiquitin-conjugating enzyme E2L 3 | 2.61 | 0.00343347 |
| serpin peptidase inhibitor, clade B (ovalbumin), member | 2.60 | 0.0030439 |
| ATPase, Ca++ transporting, plasma membrane 4 | 2.60 | 0.023011 |
| TPX2, microtubule-associated, homolog (Xenopus laevis) | 2.60 | 0.0253137 |
| thyroid hormone receptor interactor 13 | 2.59 | 0.0118319 |
| H2A histone family, member Z | 2.59 | 0.0129697 |
| CDC28 protein kinase regulatory subunit 1B | 2.57 | 0.0107391 |
| cell division cycle associated 3 | 2.57 | 0.006289 |
| minichromosome maintenance complex component 8 | 2.57 | 0.000841489 |
| E2F transcription factor 2 | 2.55 | 0.0496479 |
| TIMELESS interacting protein | 2.55 | 0.00771062 |
| minichromosome maintenance complex component 4 | 2.54 | 0.00342054 |
| polo-like kinase 4 (Drosophila) | 2.53 | 0.00209633 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| kinesin family member C1 | 2.53 | 0.00821937 |
| dihydrofolate reductase | 2.52 | 0.00307793 |
| glycerol-3-phosphate dehydrogenase 2 (mitochondrial) | 2.52 | 0.00211969 |
| TGF beta-inducible nuclear protein 1 | 2.51 | 0.0365579 |
| integrin, alpha 2 (CD49B, alpha 2 subunit of VLA-2 receptor | 2.51 | 0.0210165 |
| MLF1 interacting protein | 2.51 | 0.0177203 |
| heat shock 70 kDa protein 2 | 2.50 | 0.0215102 |
| hairy and enhancer of split 1, (*Drosophila*) | 2.50 | 0.000283509 |
| ATP-binding cassette, sub-family C (CFTR | 2.49 | 0.00382491 |
| serglycin | 2.48 | 0.0443487 |
| sema domain, immunoglobulin domain (Ig), short basic doma | 2.47 | 0.008548 |
| ankyrin repeat domain 1 (cardiac muscle) | 2.47 | 0.00911953 |
| transporter 1, ATP-binding cassette, sub-family B (MDR | 2.47 | 0.00859077 |
| transporter 1, ATP-binding cassette, sub-family B (MDR | 2.47 | 0.00859077 |
| transporter 1, ATP-binding cassette, sub-family B (MDR | 2.47 | 0.00859077 |
| histone cluster 1, H1b | 2.46 | 0.0470898 |
| family with sequence similarity 72, member A | 2.46 | 0.00165234 |
| membrane bound O-acyltransferase domain containing 1 | 2.46 | 0.01185 |
| epidermal growth factor receptor pathway substrate 8 | 2.45 | 0.0194949 |
| ASF1 anti-silencing function 1 homolog B (*S. cerevisiae*) | 2.45 | 0.00543408 |
| dedicator of cytokinesis 11 | 2.44 | 0.00697577 |
| family with sequence similarity 72, member A | 2.44 | 0.00162905 |
| actin related protein 2 | 2.44 | 0.000288443 |
| CTP synthase | 2.43 | 8.80E−05 |
| M-phase phosphoprotein 1 | 2.43 | 0.0271814 |
| CDC28 protein kinase regulatory subunit 1B | 2.43 | 0.0145263 |
| histone cluster 1, H2ai | 2.43 | 0.0161621 |
| high-mobility group nucleosomal binding domain 2 | 2.42 | 0.0030536 |
| heat shock 70 kDa protein 1A | 2.42 | 0.00734287 |
| heat shock 70 kDa protein 1A | 2.42 | 0.00674816 |
| carnitine palmitoyltransferase 1A (liver) | 2.41 | 0.00170894 |
| neurofilament, medium polypeptide 150 kDa | 2.41 | 0.0190611 |
| transmembrane protein 62 | 2.41 | 0.00761064 |
| vaccinia related kinase 1 | 2.40 | 0.0233182 |
| geminin, DNA replication inhibitor | 2.40 | 0.00167629 |
| phosphoglucomutase 2 | 2.40 | 0.00818204 |
| lamin B1 | 2.40 | 0.0477748 |
| keratin 18 | 2.40 | 0.000112551 |
| deafness, autosomal dominant 5 | 2.39 | 0.00235481 |
| proteasome (prosome, macropain) subunit, beta type, 9 (lar | 2.39 | 0.0202595 |
| proteasome (prosome, macropain) subunit, beta type, 9 (lar | 2.39 | 0.0202595 |
| proteasome (prosome, macropain) subunit, beta type, 9 (lar | 2.39 | 0.0202595 |
| chromosome 12 open reading frame 31 | 2.39 | 0.0173089 |
| isocitrate dehydrogenase 3 (NAD+) alpha | 2.39 | 0.00297129 |
| forkhead box M1 | 2.38 | 0.0203154 |
| transmembrane protein 106C | 2.38 | 0.000214223 |
| hypothetical protein LOC729012 | 2.38 | 0.000446087 |
| PHD finger protein 1 | 2.37 | 0.010191 |
| mitochondrial ribosomal protein L15 | 2.37 | 0.0306092 |
| elastin microfibril interfacer 2 | 2.37 | 0.0192072 |
| hypothetical protein DKFZp762E1312 | 2.37 | 0.00726778 |
| retinoblastoma-like 1 (p107) | 2.36 | 0.00319946 |
| tissue factor pathway inhibitor (lipoprotein-associated | 2.36 | 0.0356227 |
| epithelial cell transforming sequence 2 oncogene | 2.36 | 0.000571152 |
| crystallin, zeta (quinone reductase) | 2.36 | 0.0370884 |
| hect domain and RLD 4 | 2.36 | 0.00679184 |
| high-mobility group nucleosomal binding domain 2 | 2.36 | 0.00384071 |
| cell division cycle 25 homolog A (*S. pombe*) | 2.36 | 0.000341692 |
| thymopoietin | 2.35 | 0.0223176 |
| interferon-induced protein with tetratricopeptide repeats | 2.34 | 0.0177928 |
| Bloom syndrome | 2.34 | 0.0209259 |
| dual specificity phosphatase 1 | 2.34 | 0.00211272 |
| elongation factor, RNA polymerase II, 2 | 2.34 | 0.0130017 |
| small nuclear ribonucleoprotein D1 polypeptide 16 kDa | 2.34 | 0.0334665 |
| CDC45 cell division cycle 45-like (*S. cerevisiae*) | 2.33 | 0.00735977 |
| exonuclease 1 | 2.33 | 0.00739393 |
| ribosomal protein L39-like | 2.33 | 0.00429384 |
| histone cluster 1, H2bh | 2.33 | 0.0377748 |
| ribonucleotide reductase M1 polypeptide | 2.33 | 0.000170076 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| sulfiredoxin 1 homolog (*S. cerevisiae*) | 2.32 | 5.14E−05 |
| multiple coagulation factor deficiency 2 | 2.31 | 0.0116892 |
| proteasome (prosome, macropain) subunit, alpha type, 3 | 2.31 | 0.0195874 |
| ribonuclease H2, subunit A | 2.30 | 0.00669936 |
| minichromosome maintenance complex component 10 | 2.29 | 0.0037925 |
| heat shock 70 kDa protein 1B | 2.28 | 0.0048959 |
| heat shock 70 kDa protein 1B | 2.28 | 0.0054404 |
| heat shock 70 kDa protein 1B | 2.28 | 0.0054404 |
| ATPase, Na+ | 2.28 | 0.000381464 |
| hypothetical protein LOC201725 | 2.28 | 0.000313319 |
| cathepsin L1 | 2.27 | 0.0314419 |
| cell division cycle associated 5 | 2.27 | 0.01021 |
| RAB8B, member RAS oncogene family | 2.27 | 0.00417066 |
| SPC24, NDC80 kinetochore complex component, homolog (S. ce | 2.27 | 0.00287227 |
| gamma-glutamyl hydrolase (conjugase, folylpolygammaglutamyl | 2.26 | 0.0195219 |
| cell division cycle 25 homolog C (*S. pombe*) | 2.25 | 0.0169914 |
| mutS homolog 2, colon cancer, nonpolyposis type 1 (*E. coli*) | 2.25 | 0.00578953 |
| metallothionein 1L (gene | 2.25 | 0.00709646 |
| RRS1 ribosome biogenesis regulator homolog (*S. cerevisiae*) | 2.24 | 0.0120061 |
| cell division cycle associated 8 | 2.24 | 0.00619878 |
| shugoshin-like 2 (*S. pombe*) | 2.24 | 0.000852557 |
| mRNA turnover 4 homolog (*S. cerevisiae*) | 2.24 | 0.00373104 |
| ST6 (alpha-N-acetyl-neuraminyl-2,3-beta-galactosyl-1, | 2.24 | 0.00830766 |
| v-ets erythroblastosis virus E26 oncogene homolog 2 (avian) | 2.23 | 0.0364123 |
| replication factor C (activator 1) 2, 40 kDa | 2.23 | 0.00768959 |
| NIMA (never in mitosis gene a)-related kinase 7 | 2.23 | 0.00159114 |
| basic leucine zipper and W2 domains 2 | 2.23 | 0.0190782 |
| histone cluster 1, H2bf | 2.23 | 0.0124279 |
| eukaryotic translation initiation factor 1A, X-linked | 2.23 | 0.00330183 |
| transporter 1, ATP-binding cassette, sub-family B (MDR | 2.22 | 0.0164234 |
| transporter 1, ATP-binding cassette, sub-family B (MDR | 2.22 | 0.0164234 |
| transporter 1, ATP-binding cassette, sub-family B (MDR | 2.22 | 0.0164234 |
| polymerase (RNA) III (DNA directed) polypeptide G (32 kD) | 2.22 | 0.0298794 |
| phosphatidylinositol-4-phosphate 5-kinase, type II, alph | 2.22 | 0.00964099 |
| proteasome (prosome, macropain) 26S subunit, ATPase, 6 | 2.22 | 0.024269 |
| pituitary tumor-transforming 1 | 2.21 | 0.0485166 |
| histone cluster 2, H3d | 2.21 | 0.0102932 |
| sulfide quinone reductase-like (yeast) | 2.21 | 0.0473641 |
| serglycin | 2.20 | 0.00880325 |
| ribosomal protein L22-like 1 | 2.20 | 0.00335381 |
| membrane protein, palmitoylated 1, 55 kDa | 2.20 | 0.000396285 |
| solute carrier family 24 (sodium | 2.20 | 0.0328774 |
| STAM binding protein-like 1 | 2.20 | 0.0181743 |
| WD repeat and HMG-box DNA binding protein 1 | 2.20 | 0.0034833 |
| CSE1 chromosome segregation 1-like (yeast) | 2.20 | 0.0013662 |
| origin recognition complex, subunit 6 like (yeast) | 2.20 | 0.00182466 |
| transcription factor A, mitochondrial | 2.19 | 0.0110092 |
| exosome component 8 | 2.19 | 0.00132017 |
| mitochondrial ribosomal protein L1 | 2.19 | 0.0361058 |
| sphingomyelin synthase 2 | 2.19 | 0.0020701 |
| deoxycytidine kinase | 2.18 | 0.00101444 |
| family with sequence similarity 29, member A | 2.18 | 0.00469407 |
| chromosome 6 open reading frame 167 | 2.18 | 0.0011095 |
| dual specificity phosphatase 11 (RNA | 2.18 | 0.00426788 |
| F-box protein 45 | 2.18 | 0.00510098 |
| ras-related C3 botulinum toxin substrate 2 (rho family, sma | 2.17 | 0.0292466 |
| FK506 binding protein 5 | 2.17 | 0.0193805 |
| breast cancer 1, early onset | 2.17 | 0.0180553 |
| nuclear factor I | 2.17 | 0.0010313 |
| thioredoxin | 2.17 | 0.009636 |
| SH2 domain containing 4A | 2.16 | 0.0323646 |
| TGF beta-inducible nuclear protein 1 | 2.16 | 0.00285964 |
| PSMC3 interacting protein | 2.16 | 0.00766442 |
| chromosome 3 open reading frame 14 | 2.15 | 0.0377617 |
| polycomb group ring finger 5 | 2.15 | 0.000294142 |
| centrosomal protein 27 kDa | 2.15 | 0.00931602 |
| family with sequence similarity 64, member A | 2.14 | 0.0019785 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| acidic (leucine-rich) nuclear phosphoprotein 32 family, m | 2.14 | 0.0300263 |
| sterol O-acyltransferase (acyl-Coenzyme A: cholesterol acy | 2.14 | 0.0193637 |
| TATA box binding protein (TBP)-associated factor, RNA poly | 2.13 | 0.00514451 |
| origin recognition complex, subunit 5-like (yeast) | 2.13 | 0.049697 |
| Rac GTPase activating protein 1 pseudogene | 2.13 | 0.000269488 |
| LSM5 homolog, U6 small nuclear RNA associated (S. cerevisia | 2.13 | 0.00264664 |
| minichromosome maintenance complex component 7 | 2.13 | 0.0457691 |
| met proto-oncogene (hepatocyte growth factor receptor) | 2.13 | 0.0318147 |
| tripartite motif-containing 25 | 2.13 | 0.0456344 |
| chromosome 13 open reading frame 34 | 2.13 | 0.000702936 |
| patatin-like phospholipase domain containing 4 | 2.13 | 0.0168306 |
| minichromosome maintenance complex component 6 | 2.12 | 0.0161279 |
| intraflagellar transport 80 homolog (*Chlamydomonas*) | 2.12 | 0.0247286 |
| peptidylprolyl isomerase F (cyclophilin F) | 2.12 | 0.00093846 |
| UTP15, U3 small nucleolar ribonucleoprotein, homolog (S. c | 2.12 | 0.00482559 |
| TAF9B RNA polymerase II, TATA box binding protein (TBP)-as | 2.12 | 0.0170365 |
| TAF9B RNA polymerase II, TATA box binding protein (TBP)-as | 2.12 | 0.0170365 |
| ecotropic viral integration site 2B | 2.12 | 0.0171408 |
| 3'-phosphoadenosine 5'-phosphosulfate synthase 2 | 2.12 | 1.43E−05 |
| proteasome (prosome, macropain) activator subunit 2 (PA28 | 2.12 | 0.00609885 |
| ADAM metallopeptidase with thrombospondin type 1 motif, | 2.12 | 0.0102751 |
| flap structure-specific endonuclease 1 | 2.12 | 0.006882 |
| S100 calcium binding protein A3 | 2.12 | 0.0324073 |
| RAD18 homolog (*S. cerevisiae*) | 2.11 | 0.0016685 |
| minichromosome maintenance complex component 3 | 2.11 | 0.0018389 |
| exosome component 3 | 2.11 | 0.0249115 |
| cysteinyl-tRNA synthetase 2, mitochondrial (putative) | 2.11 | 0.00564558 |
| glutamate-cysteine ligase, modifier subunit | 2.11 | 0.00378868 |
| brix domain containing 1 | 2.11 | 0.00981178 |
| kinesin family member 22 | 2.11 | 0.0192406 |
| UTP11-like, U3 small nucleolar ribonucleoprotein, (yeast) | 2.10 | 0.0132794 |
| v-ral simian leukemia viral oncogene homolog B (ras related | 2.10 | 0.012225 |
| meiotic nuclear divisions 1 homolog (*S. cerevisiae*) | 2.10 | 0.00164447 |
| phenylalanyl-tRNA synthetase, beta subunit | 2.10 | 0.000245973 |
| similar to Ubiquitin-conjugating enzyme E2S (Ubiqui | 2.10 | 0.000415822 |
| coiled-coil domain containing 68 | 2.10 | 0.00227586 |
| lamin B receptor | 2.10 | 0.000151784 |
| Niemann-Pick disease, type C1 | 2.10 | 0.0108117 |
| hydroxysteroid dehydrogenase like 2 | 2.09 | 3.71E−05 |
| RMI1, RecQ mediated genome instability 1, homolog (S. cerev | 2.09 | 0.00294705 |
| overexpressed in colon carcinoma-1 | 2.09 | 0.015322 |
| hypothetical protein FLJ20425 | 2.09 | 0.0174225 |
| primase, polypeptide 1, 49 kDa | 2.09 | 0.00801018 |
| chromosome 20 open reading frame 121 | 2.09 | 0.0146323 |
| microtubule associated serine | 2.08 | 0.00536974 |
| endothelial differentiation, sphingolipid G-protein-coupled | 2.08 | 0.0132848 |
| homeobox A9 | 2.08 | 0.00520942 |
| centromere protein L | 2.08 | 0.000880856 |
| nucleolar complex associated 3 homolog (*S. cerevisiae*) | 2.07 | 0.000373346 |
| fibroblast growth factor 7 (keratinocyte growth factor) | 2.07 | 0.0173208 |
| cysteine rich transmembrane BMP regulator 1 (chordin-like) | 2.07 | 0.0267286 |
| nucleoporin 155 kDa | 2.07 | 0.00218453 |
| FLJ20105 protein | 2.06 | 0.0127979 |
| CD44 molecule (Indian blood group) | 2.06 | 0.000651436 |
| polymerase (DNA directed), alpha 2 (70 kD subunit) | 2.06 | 0.0033903 |
| v-myb myeloblastosis viral oncogene homolog (avian)-like 2 | 2.06 | 0.00989416 |
| origin recognition complex, subunit 1-like (yeast) | 2.06 | 0.00207753 |
| hypothetical protein FLJ25416 | 2.06 | 0.000177531 |
| kinesin family member 22 | 2.06 | 0.0242075 |
| heat shock 60 kDa protein 1 (chaperonin) | 2.06 | 0.0327412 |
| minichromosome maintenance complex component 2 | 2.05 | 0.0021347 |
| fumarylacetoacetate hydrolase (fumarylacetoacetase) | 2.05 | 3.88E−05 |
| glycerol kinase 3 pseudogene | 2.05 | 0.0103203 |
| retinitis pigmentosa 2 (X-linked recessive) | 2.05 | 0.0264185 |

TABLE 2-continued

Gene expression in 2D adherent cells of the present invention
compared to those expressed by PLX of WO/2007/108003

| Gene | 2D vs. Plurix (fold change) | p-value (treat) |
|---|---|---|
| U2AF homology motif (UHM) kinase 1 | 2.05 | 0.0255167 |
| chaperonin containing TCP1, subunit 5 (epsilon) | 2.04 | 0.00125909 |
| ATPase, H+ transporting, lysosomal 34 kDa, V1 subunit D | 2.04 | 0.0317453 |
| transcription termination factor, RNA polymerase II | 2.04 | 0.000393489 |
| succinate-CoA ligase, GDP-forming, beta subunit | 2.04 | 0.0028167 |
| cyclin-dependent kinase inhibitor 1B (p27, Kip1) | 2.04 | 0.00183021 |
| tyrosine 3-monooxygenase | 2.04 | 0.00021508 |
| cofactor required for Sp1 transcriptional activation, subu | 2.04 | 0.00141809 |
| glycosyltransferase 8 domain containing 3 | 2.03 | 0.022868 |
| ribosomal RNA processing 15 homolog (*S. cerevisiae*) | 2.03 | 0.0274884 |
| glycogenin 1 | 2.03 | 0.0224317 |
| hypothetical protein FLJ40869 | 2.03 | 0.00444509 |
| proliferating cell nuclear antigen | 2.03 | 0.0031727 |
| sterile alpha motif domain containing 12 | 2.03 | 0.0232188 |
| chromosome 16 open reading frame 59 | 2.03 | 0.00185191 |
| cofilin 2 (muscle) | 2.03 | 0.0459235 |
| eukaryotic translation initiation factor 2, subunit 2 bet | 2.03 | 0.0139947 |
| chromatin assembly factor 1, subunit B (p60) | 2.03 | 0.0119687 |
| Zwilch, kinetochore associated, homolog (*Drosophila*) | 2.02 | 0.000725107 |
| ATP-binding cassette, sub-family E (OABP), member 1 | 2.02 | 0.00454751 |
| LSM3 homolog, U6 small nuclear RNA associated (S. cerevisia | 2.02 | 0.0199824 |
| IQ motif containing GTPase activating protein 3 | 2.02 | 0.0495882 |
| tubulin, alpha 1c | 2.02 | 0.00862586 |
| DBF4 homolog (*S. cerevisiae*) | 2.01 | 0.0458795 |
| amyloid beta precursor protein binding protein 1 | 2.01 | 0.000910538 |
| suppressor of variegation 3-9 homolog 1 (*Drosophila*) | 2.01 | 0.00224324 |
| THO complex 7 homolog (*Drosophila*) | 2.01 | 0.0047251 |
| amyotrophic lateral sclerosis 2 (juvenile) chromosome re | 2.01 | 0.0484466 |
| nucleoporin 37 kDa | 2.01 | 0.00652747 |
| nucleolar protein 11 | 2.01 | 0.000852662 |
| ATP synthase, H+ transporting, mitochondrial F0 complex | 2.01 | 0.00866627 |
| histone cluster 1, H2ai | 2.01 | 0.0129155 |
| phytoceramidase, alkaline | 2.01 | 0.0157729 |
| primase, polypeptide 2A, 58 kDa | 2.01 | 0.00290097 |
| similar to High mobility group protein B1 (High mobili | 2.00 | 0.000363158 |
| mastermind-like 3 (*Drosophila*) | −2.00 | 0.00386667 |
| UDP-N-acetyl-alpha-D-galactosamine:polypeptide N-acetylga | −2.01 | 0.0268634 |
| ring finger protein 122 | −2.01 | 0.0236621 |
| chromodomain helicase DNA binding protein 3 | −2.01 | 6.39E−05 |
| centaurin, gamma-like family, member 10 pseudogene | −2.01 | 8.70E−05 |
| chromosome 7 open reading frame 10 | −2.01 | 0.00738442 |
| chromosome 6 open reading frame 111 | −2.01 | 0.0104492 |
| centaurin, gamma-like family, member 10 pseudogene | −2.01 | 0.000334818 |
| Prader-Willi syndrome chromosome region 1 | −2.01 | 0.0415526 |
| KIAA1245 | −2.01 | 0.0186309 |
| peroxidasin homolog (*Drosophila*) | −2.01 | 0.00219049 |
| melanoma antigen family D, 4 | −2.02 | 0.0263076 |
| melanoma antigen family D, 4 | −2.02 | 0.0263076 |
| glucosidase, alpha; acid (Pompe disease, glycogen storage di | −2.02 | 0.000418401 |
| phospholipase A2 receptor 1, 180 kDa | −2.03 | 0.00069343 |
| glycosyltransferase 8 domain containing 2 | −2.03 | 0.0173546 |
| KIAA1546 | −2.03 | 0.000255634 |
| protocadherin beta 9 | −2.03 | 0.0285124 |
| TBC1 domain family, member 3B | −2.03 | 0.000414974 |
| sushi, nidogen and EGF-like domains 1 | −2.03 | 0.00161129 |
| microtubule-actin crosslinking factor 1 | −2.04 | 0.00216 |
| region containing neuroblastoma breakpoint family, | −2.04 | 0.0213393 |
| golgi autoantigen, golgin subfamily a-like pseudogene | −2.04 | 0.0182674 |
| transducin-like enhancer of split 4 (E(sp1) homolog, Drosop | −2.04 | 0.0164153 |
| solute carrier family 22 (organic cation transporter), | −2.05 | 0.0137275 |
| neighbor of Punc E11 | −2.05 | 0.0184739 |
| insulin-like growth factor binding protein 5 | −2.05 | 0.011614 |
| KIAA1245 | −2.06 | 0.0185376 |
| vitamin D (1,25-dihydroxyvitamin D3) receptor | −2.06 | 0.000192208 |
| B-cell CLL | −2.06 | 0.00343507 |
| KIAA1305 | −2.06 | 0.00813727 |
| KIAA1245 | −2.06 | 0.0185609 |
| centaurin, gamma-like family, member 10 pseudogene | −2.07 | 3.08E−05 |
| TBC1 domain family, member 3B | −2.07 | 0.00141297 |
| similar to TBC1 domain family member 3 (Rab GTPase- | −2.08 | 0.00105098 |
| mannosidase, alpha, class 2B, member 1 | −2.08 | 0.000353303 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| cysteine-rich PAK1 inhibitor | −2.08 | 0.000125336 |
| midline 1 (Opitz | −2.08 | 0.00130803 |
| small nucleolar RNA, H | −2.09 | 0.017124 |
| urocortin 2 | −2.09 | 0.00172263 |
| neuroblastoma breakpoint family, member 11 | −2.09 | 0.0138065 |
| collagen, type VI, alpha 3 | −2.09 | 2.09E−06 |
| neuroblastoma breakpoint family, member 11 | −2.09 | 0.0148372 |
| hypothetical protein LOC646870 | −2.09 | 0.0117625 |
| calsyntenin 3 | −2.09 | 0.00300887 |
| cortactin binding protein 2 | −2.09 | 2.28E−05 |
| synaptic vesicle glycoprotein 2A | −2.10 | 0.00704212 |
| similar to Dynamin-1 (D100) (Dynamin, brain) (B-dyn | −2.10 | 0.0190733 |
| similar to Dynamin-1 (D100) (Dynamin, brain) (B-dyn | −2.10 | 0.0190733 |
| similar to TBC1 domain family member 3 (Rab GTPase- | −2.10 | 0.00108467 |
| Notch homolog 2 (*Drosophila*) N-terminal like | −2.10 | 0.0193058 |
| matrix-remodelling associated 5 | −2.11 | 0.000317637 |
| complement component 1, s subcomponent | −2.11 | 0.0395863 |
| cysteine sulfinic acid decarboxylase | −2.11 | 0.00428211 |
| hypothetical protein FLJ36144 | −2.11 | 0.00958437 |
| hypothetical protein FLJ36144 | −2.11 | 0.00958437 |
| dihydropyrimidinase-like 3 | −2.12 | 0.0165203 |
| procollagen C-endopeptidase enhancer | −2.12 | 0.0039236 |
| golgi autoantigen, golgin subfamily a-like pseudogene | −2.12 | 0.00720508 |
| TBC1 domain family, member 3B | −2.12 | 0.00122924 |
| collagen, type VII, alpha 1 (epidermolysis bullosa, dystr | −2.13 | 0.00109233 |
| versican | −2.14 | 0.023885 |
| mannose receptor, C type 2 | −2.14 | 0.00012142 |
| golgi autoantigen, golgin subfamily a-like pseudogene | −2.14 | 0.00767095 |
| dynamin 1 | −2.15 | 0.00139674 |
| TBC1 domain family, member 3B | −2.16 | 0.00130459 |
| PHD finger protein 21A | −2.17 | 0.00980401 |
| centaurin, gamma-like family, member 10 pseudogene | −2.17 | 0.000180846 |
| slit homolog 3 (*Drosophila*) | −2.17 | 0.02844 |
| neuroepithelial cell transforming gene 1 | −2.18 | 0.0109689 |
| cyclin L2 | −2.18 | 0.00093459 |
| similar to dJ402H5.2 (novel protein similar to wo | −2.18 | 0.00621503 |
| phospholipase D family, member 3 | −2.18 | 1.17E−05 |
| collagen, type VIII, alpha 1 | −2.19 | 0.00187242 |
| cyclin L2 | −2.19 | 0.00109621 |
| protocadherin beta 14 | −2.20 | 0.0103892 |
| matrix metallopeptidase 2 (gelatinase A, 72 kDa gelatinase, | −2.20 | 5.59E−05 |
| lysyl oxidase-like 4 | −2.21 | 0.0120148 |
| golgi autoantigen, golgin subfamily a-like pseudogene | −2.21 | 0.00977719 |
| WW domain containing transcription regulator 1 | −2.21 | 0.0379899 |
| PDZ domain containing RING finger 3 | −2.21 | 0.00931014 |
| chromosome 14 open reading frame 37 | −2.21 | 0.0182453 |
| brain and acute leukemia, cytoplasmic | −2.22 | 0.0476919 |
| calcium channel, voltage-dependent, L type, alpha 1C sub | −2.22 | 0.0189661 |
| jun oncogene | −2.23 | 7.21E−05 |
| interleukin 19 | −2.23 | 0.0310328 |
| centaurin, gamma-like family, member 10 pseudogene | −2.23 | 0.000595086 |
| centaurin, gamma-like family, member 10 pseudogene | −2.23 | 0.000595086 |
| — | −2.24 | 0.00666187 |
| golgi autoantigen, golgin subfamily b, macrogolgin (with | −2.24 | 0.0164005 |
| chromosome 15 open reading frame 51 | −2.24 | 0.0123547 |
| similar to Dynamin-1 (D100) (Dynamin, brain) (B-dyn | −2.24 | 0.0123547 |
| similar to Dynamin-1 (D100) (Dynamin, brain) (B-dyn | −2.24 | 0.0123547 |
| AE binding protein 1 | −2.25 | 0.000105628 |
| golgi autoantigen, golgin subfamily a-like pseudogene | −2.26 | 0.00770626 |
| transmembrane protein 16A | −2.27 | 0.0481085 |
| hypothetical LOC399844 | −2.27 | 0.000491694 |
| oculomedin | −2.27 | 0.00778869 |
| low density lipoprotein-related protein 1 (alpha-2-macroglo | −2.28 | 4.26E−05 |
| fibronectin leucine rich transmembrane protein 2 | −2.28 | 0.0135122 |
| phospholipid transfer protein | −2.29 | 0.00999206 |
| similar to Dynamin-1 (D100) (Dynamin, brain) (B-dyn | −2.29 | 0.0122573 |
| SATB homeobox 2 | −2.31 | 0.039781 |
| similar to TBC1 domain family member 3 (Rab GTPase- | −2.32 | 0.000870285 |
| tweety homolog 1 (*Drosophila*) | −2.32 | 0.00450824 |
| CD24 molecule | −2.34 | 0.0340122 |
| chimerin (chimaerin) 1 | −2.35 | 0.0287031 |
| AHA1, activator of heat shock 90 kDa protein ATPase homolog | −2.37 | 0.00979472 |

TABLE 2-continued

Gene expression in 2D adherent cells of the present invention compared to those expressed by PLX of WO/2007/108003

| Gene | 2D vs. Plurix (fold change) | p-value (treat) |
|---|---|---|
| bicaudal C homolog 1 (*Drosophila*) | −2.38 | 0.0347162 |
| solute carrier family 6 (neurotransmitter transporter, ta | −2.38 | 0.00729635 |
| milk fat globule-EGF factor 8 protein | −2.39 | 0.000987073 |
| WNK lysine deficient protein kinase 1 | −2.40 | 1.57E−05 |
| small nucleolar RNA, H | −2.41 | 0.00843141 |
| tweety homolog 3 (*Drosophila*) | −2.42 | 0.000165552 |
| SH3 and PX domains 2B | −2.42 | 0.0244357 |
| WD repeat and SOCS box-containing 1 | −2.44 | 0.0387851 |
| hypothetical protein PRO2012 | −2.45 | 0.00756704 |
| golgi autoantigen, golgin subfamily a-like pseudogene | −2.46 | 0.00320764 |
| microfibrillar-associated protein 2 | −2.47 | 0.0152901 |
| collagen, type XII, alpha 1 | −2.47 | 0.000204664 |
| ST6 beta-galactosamide alpha-2,6-sialyltranferase 2 | −2.47 | 0.0216987 |
| thioredoxin interacting protein | −2.48 | 0.0135494 |
| latent transforming growth factor beta binding protein 2 | −2.49 | 4.08E−05 |
| golgi autoantigen, golgin subfamily a-like pseudogene | −2.49 | 0.00603583 |
| formin binding protein 1-like | −2.50 | 0.00290401 |
| maternally expressed 3 | −2.52 | 0.0112259 |
| PTK7 protein tyrosine kinase 7 | −2.54 | 0.000116114 |
| ribonuclease P RNA component H1 | −2.57 | 0.0156126 |
| sushi-repeat-containing protein, X-linked 2 | −2.58 | 0.0253856 |
| sortilin-related VPS10 domain containing receptor 2 | −2.58 | 0.00936311 |
| similar to RIKEN cDNA 1110018M03 | −2.59 | 0.00516476 |
| pyridoxal-dependent decarboxylase domain containing 2 | −2.60 | 0.00683647 |
| Enah | −2.61 | 0.0077547 |
| asporin | −2.62 | 0.000659873 |
| small Cajal body-specific RNA 17 | −2.63 | 0.0301336 |
| nuclear pore complex interacting protein | −2.67 | 0.00988632 |
| sushi, von Willebrand factor type A, EGF and pentraxin dom | −2.69 | 2.23E−05 |
| protein tyrosine phosphatase, receptor type, U | −2.69 | 0.0270428 |
| collagen, type V, alpha 1 | −2.70 | 0.0166427 |
| nuclear pore complex interacting protein | −2.73 | 0.0018339 |
| transformer-2 alpha | −2.74 | 0.012256 |
| dystrophin related protein 2 | −2.79 | 0.0137557 |
| golgi autoantigen, golgin subfamily a, 8A | −2.80 | 0.0111179 |
| collagen, type VI, alpha 2 | −2.81 | 0.0149554 |
| transforming growth factor, beta 3 | −2.81 | 0.0287865 |
| trophinin | −2.82 | 0.00298044 |
| hypothetical protein MGC24103 | −2.86 | 0.0346673 |
| supervillin | −2.87 | 0.0412717 |
| ADAM metallopeptidase with thrombospondin type 1 motif, | −2.90 | 0.0113968 |
| kinesin family member 26B | −2.91 | 0.00363199 |
| nuclear pore complex interacting protein | −2.91 | 0.00160273 |
| trichorhinophalangeal syndrome I | −2.94 | 0.00557712 |
| nuclear pore complex interacting protein | −2.96 | 0.00111223 |
| small nucleolar RNA, C | −2.96 | 0.00666866 |
| homeobox A2 | −2.97 | 0.0435423 |
| distal-less homeobox 5 | −3.00 | 0.000640157 |
| dachsous 1 (*Drosophila*) | −3.00 | 0.00697244 |
| small nucleolar RNA, C | −3.06 | 0.0274043 |
| small nucleolar RNA, C | −3.06 | 0.0274043 |
| nuclear pore complex interacting protein | −3.09 | 0.00583397 |
| small nucleolar RNA, C | −3.14 | 0.0104491 |
| small nucleolar RNA, C | −3.14 | 0.0104491 |
| sushi-repeat-containing protein, X-linked | −3.16 | 0.00370941 |
| zinc finger protein 521 | −3.17 | 0.00668815 |
| nuclear pore complex interacting protein | −3.17 | 0.00117582 |
| chromosome 9 open reading frame 3 | −3.18 | 0.00410177 |
| golgi autoantigen, golgin subfamily a, 8B | −3.18 | 0.0121417 |
| hemicentin 1 | −3.21 | 0.0461603 |
| small nucleolar RNA, C | −3.24 | 0.00765575 |
| Kallmann syndrome 1 sequence | −3.25 | 0.000548703 |
| tenascin C (hexabrachion) | −3.26 | 8.26E−05 |
| nuclear pore complex interacting protein | −3.29 | 0.00282604 |
| nuclear pore complex interacting protein | −3.34 | 0.00263888 |
| homeobox B2 | −3.36 | 0.00665994 |
| similar to nuclear pore complex interacting protein | −3.41 | 0.0187322 |
| nuclear pore complex interacting protein | −3.46 | 0.00354416 |
| cholesterol 25-hydroxylase | −3.51 | 0.0445558 |
| ring finger protein 144 | −3.52 | 0.0135334 |
| nuclear pore complex interacting protein | −3.55 | 0.00316496 |
| calbindin 2, 29 kDa (calretinin) | −3.56 | 0.0290743 |

TABLE 2-continued

Gene expression in 2D adherent cells of the present invention
compared to those expressed by PLX of WO/2007/108003

| Gene | 2D vs. Plurix (fold change) | p-value (treat) |
|---|---|---|
| nuclear pore complex interacting protein | −3.58 | 0.00032839 |
| nuclear pore complex interacting protein | −3.60 | 0.000414309 |
| nuclear pore complex interacting protein | −3.62 | 0.00283418 |
| nuclear pore complex interacting protein | −3.64 | 0.000213956 |
| nuclear pore complex interacting protein | −3.66 | 0.000377834 |
| KIAA1641 | −3.69 | 0.0191782 |
| UDP-N-acetyl-alpha-D-galactosamine:polypeptide N-acetylga | −3.72 | 0.00964109 |
| nuclear pore complex interacting protein | −3.73 | 0.000352007 |
| leucine rich repeat containing 17 | −3.75 | 0.0263961 |
| chromosome 9 open reading frame 3 | −3.80 | 0.0233723 |
| nuclear pore complex interacting protein | −3.82 | 0.00368967 |
| neurotrimin | −3.87 | 3.78E−06 |
| protein tyrosine phosphatase, receptor type, N | −4.02 | 0.0294569 |
| KIAA1641 | −4.02 | 0.00659194 |
| — | −4.06 | 0.00488845 |
| KIAA1641 | −4.16 | 0.0170531 |
| integrin, alpha 11 | −4.16 | 0.000390317 |
| KIAA1641 | −4.27 | 0.013175 |
| odz, odd Oz | −4.28 | 0.00172671 |
| transmembrane protein 119 | −4.34 | 0.00801387 |
| plexin domain containing 2 | −4.44 | 0.031799 |
| ras homolog gene family, member J | −4.59 | 0.00197982 |
| homeobox B3 | −4.60 | 0.0354368 |
| similar to Protein KIAA0220 | −4.72 | 0.0302619 |
| raftlin family member 2 | −4.79 | 0.0260454 |
| WNT1 inducible signaling pathway protein 1 | −5.99 | 0.000672342 |
| clusterin | −6.40 | 0.0303973 |
| serpin peptidase inhibitor, clade F (alpha-2 antiplasmi | −6.47 | 0.00362941 |
| sulfatase 2 | −6.58 | 5.88E−05 |
| hephaestin | −6.74 | 0.0123141 |
| junctional adhesion molecule 2 | −7.33 | 0.0306758 |
| fibronectin type III domain containing 1 | −7.46 | 0.0334696 |
| sarcoglycan, delta (35 kDa dystrophin-associated glycoprotein | −7.69 | 0.000881984 |
| cystatin SN | −8.27 | 0.0496433 |
| microfibrillar-associated protein 4 | −8.67 | 0.00155578 |
| biglycan | −8.70 | 0.00161284 |
| transmembrane, prostate androgen induced RNA | −10.54 | 0.000100935 |
| carboxypeptidase E | −12.48 | 0.00738131 |

Figure 2:
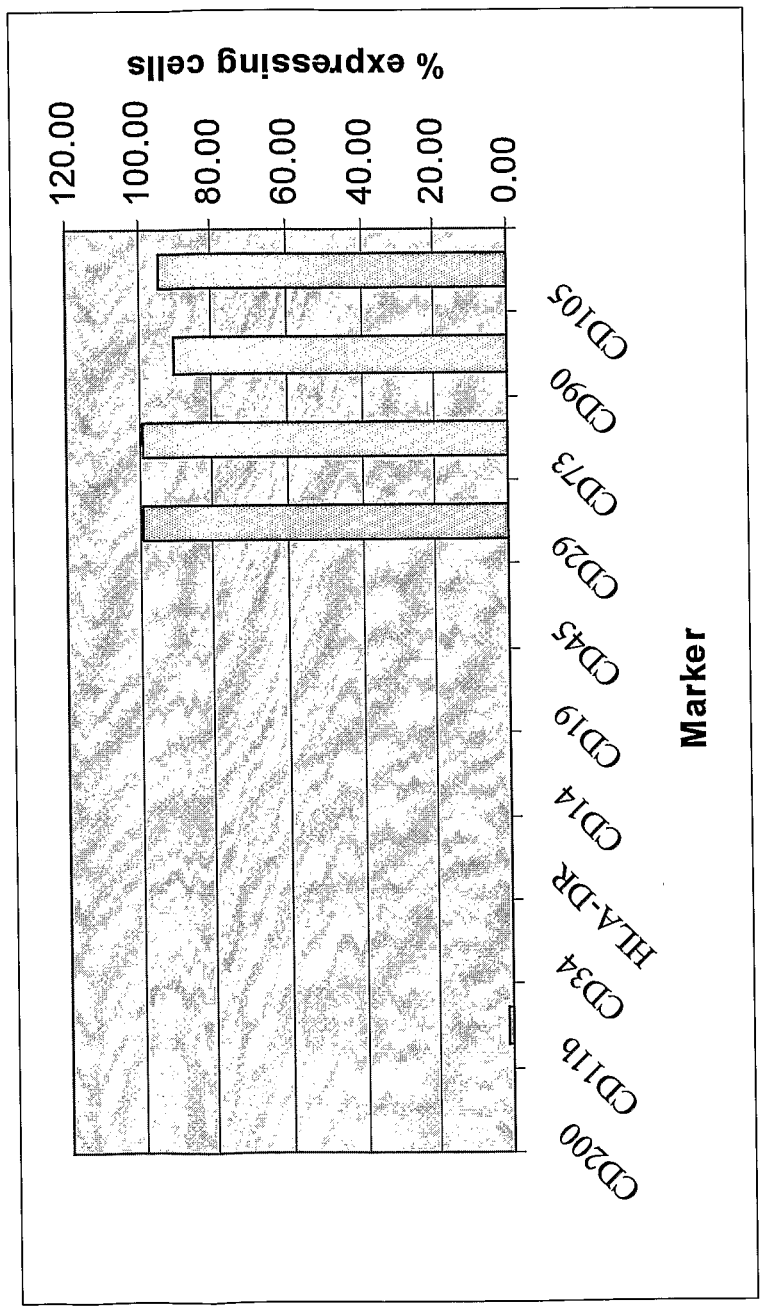
FIG. 2 is a bar graph depicting marker expression on adherent cells of placenta grown according to the present teachings. Of note, negative expression was recorded for CD11b, CD34, HLA-DR, CD14, CD19 CD200 and CD45, while positive expression was noted for CD29, CD73, CD90 and CD105.

Characterization of Membrane Markers on 2D Adherent Cells of the Present Teachings— the surface antigens expressed by 2D adherent cells were examined using monoclonal antibodies. These cells were stable adhesive cells that were expanded in vitro without the loss of phenotype and without showing signs of karyotypic changes. Flow cytometric analysis of 2D adherent cell's membrane markers showed a high incidence of cells expressing CD105, CD73, CD90 and CD29. Furthermore, a high incidence of cells was lacking the expression of CD45, CD34 and CD19, CD11b, CD14, CD200 and HLA-DR surface markers (FIG. 2).

Immunomodulation by 2D Adherent Cells—

Figure 3:
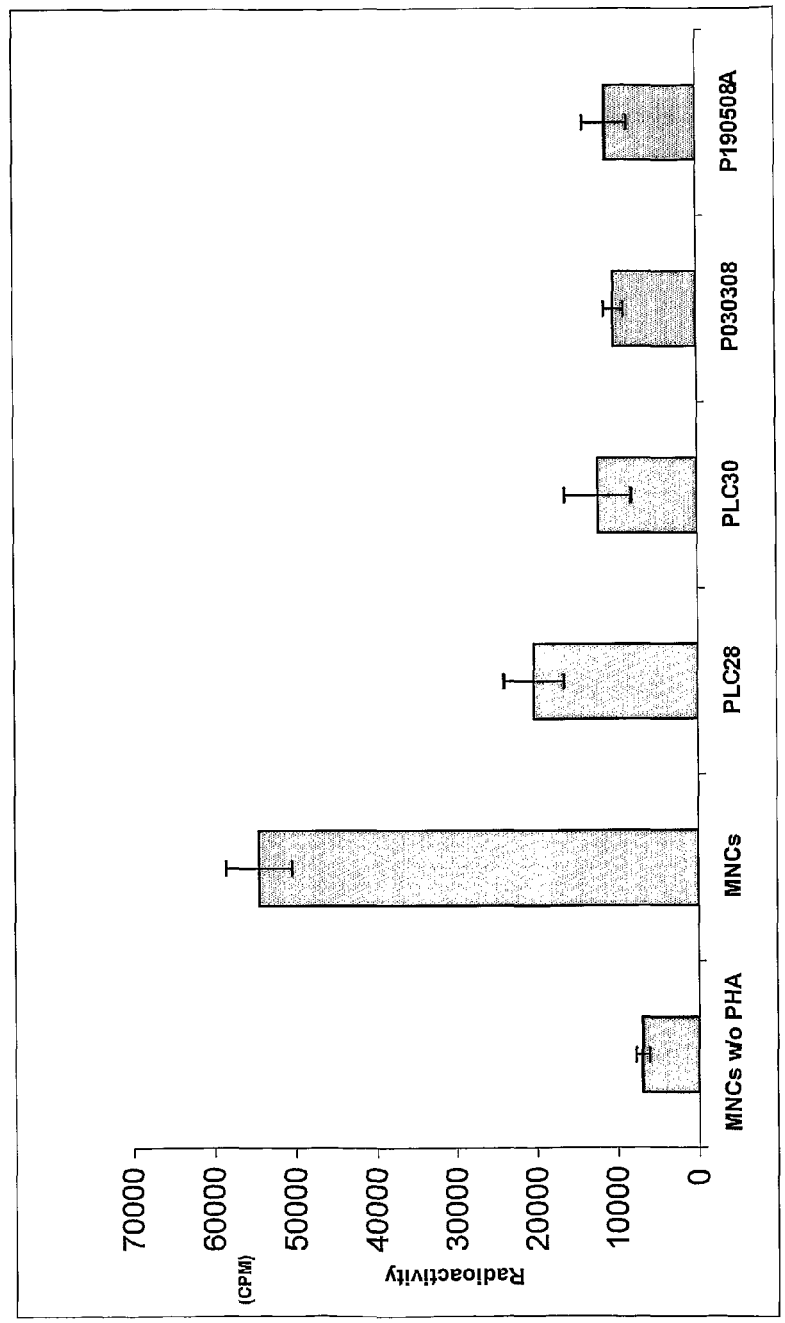
FIG. 3 is a bar graph depicting reduction of lymphocyte cell response by adherent cells of placenta grown according to the present teachings. Peripheral blood (PB) derived mononuclear cells (MNCs) were stimulated with PHA (10 µg/ml). One of four different batches of 2D adherent cells were added to the stimulated MNCs. Three replicates of each group were seeded in 96-well plates.

The immunogenicity of the 2D adherent cells was investigated next. As shown in FIG. 3, four different batches of 2D adherent cells were capable of reducing lymphocyte proliferation, following mitogenic stimuli with Phytohemagglutinin (PHA), as was measured by Thymidine incorporation.

Example 4

Osteocyte Differentiation of 2D Adherent Cells 2D adherent cells from bone marrow or placenta origin were grown under osteocyte differentiation stimulating conditions.

Materials and Experimental Methods
Osteogenesis

Osteogenesis was carried out according to Chemicon osteogenesis kit (cat no. scr028, Millipore, Mass., USA)

Osteogenesis Induction Medium

Osteogenesis induction medium was freshly made prior to each medium exchange using the kit components (See Table 3, below).

TABLE 3

Osteogenesis medium components

| Component | Stock concentration | Amount | Final con |
|---|---|---|---|
| DMEM low glucose (Invitrogen, Gibco) | | 8.7 ml | 87% |
| Serum (heat inactivated) | | 1 ml | 10% |
| dexamethasone | 1 mM | 1 µl | 0.1 µM |
| Asorbic Acid-2-Phosphate solution | 0.1M | 20 µl | 0.2 mM |
| Glycerol-2-Phosphate Solution | 1M | 100 µL | 10 Mm |
| L-glutamine | X 100 | 100 µl | X 1 |
| Pen & Strep | X 100 | 100 µl | X 1 |

To arrive at 1 mM dexamethasone solution, 900 µl ethanol was added to 100 µl dexamethasone 10 mM solution. Stock solution was stored with the rest of the kit's components at −20° C. A 50 ml serum vial was heat inactivated, divided into 5 ml aliquots and kept at −20° C. until use.

Coating 24-Well Tissue Culture Plates

A coating mixture comprising 12 µg/ml vitronectin and 12 µg/ml collagen (both included in the kit) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (p1c11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco). Placenta derived cells (4 wells×2 plates) or bone marrow derived cells (1 well×2 plates) were grown until 100% confluent (typically overnight) before initiating osteogenic differentiation.

When cells reached 100% confluence, growth medium was aspirated and replaced with 1 ml osteogenesis induction medium (differentiation day 1). Osteogenesis induction medium was replaced with fresh medium every 2-3 days for a total of 14-17 days.

As a control, one of the two plates (for each of the cell types) was not incubated with osteogenesis differentiation medium but rather with the growth medium (described hereinabove).

On day 17, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 µl) was added to the cells. Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Experimental Results

Osteocyte differentiation of placenta- or bone marrow-derived adherent cells in osteogenic induction medium resulted in differentiation of over 50% of the bone marrow cells, as demonstrated by positive alizarin red staining (FIG. 4B). On the contrary, none of the placental derived cells showed any signs of osteogenic differentiation (see FIGS. 4B and 4E and Table 4, below).

TABLE 4

Differentiation summary

|  | BM 108 + BM109 | PLC-11-3-1 | PLC-8-2-1 | Plc-15-3-4-2 | Plc 4-3-1 |
|---|---|---|---|---|---|
| Osteocytes | +++ | − | − | − | − |
| Adipocytes | +++ | − | − | − | − |

Example 5

Osteocyte Differentiation of 2D Adherent Cells in Modified Growth Medium 2D adherent cells from bone marrow or placenta origin were stimulated to differentiate in a modified osteogenic medium comprising Vitamin D and higher concentrations of dexamethasone.

Materials and Experimental Methods

Osteogenesis Induction Medium

Osteogenesis induction medium was freshly made prior to each medium exchange using the components listed in Table 5, below, along with Vitamin D.

TABLE 5

Osteogenesis medium components

| Component | Stock con | Amount | Final con |
|---|---|---|---|
| DMEM high glucose (Biological Industries, Bet Haemek, Israel) |  | 8.7 ml | 87% |
| L-glutamine | X 100 | 100 µl | X 1 |
| Serum (heat inactivated) |  | 1 ml | 10% |
| Dexamethasone (Chemicon) | 10 mM | 10 µl | 10 µM |
| Asorbic Acid-2-Phosphate solution (Chemicon) | 0.1M | 20 µl | 0.2 mM |
| Glycerol-2-Phosphate Solution (Chemicon) | 1M | 100 µL | 10 Mm |
| Vitamin D (Sigma) | 10 µM | 10 µL | 10 nM |
| Gentamycin (Biological Industries, Bet Haemek, Israel) | X 100 | 100 µl | X 1 |

A 50 ml serum vial was heat inactivated, divided into 5 ml aliquots and kept at −20° C. until use.

Coating 48-Well Tissue Culture Plates

A coating mixture comprising 12 µg/ml vitronectin and 12 µg/ml collagen (both from Chemicon) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (PLC 8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 wells×2 plates). Bone marrow derived cells (BM109) were plated (150,000 cells per well) in 0.5 ml growth medium (as described above) (1 well×2 plates). Cells were grown until 100% confluent (typically overnight) before initiating osteogenic differentiation.

When cells reached 100% confluence, growth medium was aspirated and replaced with 0.5 ml osteogenesis induction medium (differentiation day 1). Osteogenesis induction medium was replaced with fresh medium every 2-3 days for a total of 26 days.

As a control, one of the two plates (for each of the cell types) was not incubated with osteogenesis differentiation medium but rather with the growth medium (described hereinabove).

On day 26, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 μl) was added to the cells. Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Experimental Results

Osteogenic differentiation of placenta- or bone marrow-derived adherent cells was performed by modification of the protocol described in Example 4, hereinabove, according to previous teachings [Parloni et al. (2008) Stem Cells 26(2): 300-11]. The main difference between the growth conditions presented in Example 4 and the results presented herein was the addition of vitamin D to the differentiation medium and the higher concentrations of dexamethasone. As evident from the results, over 50% of the bone marrow cells underwent differentiation into osteocytes, as demonstrated by positive alizarin red staining (see FIG. 5B). However, none of the placental derived cells showed any signs of osteogenic differentiation (see FIG. 5E and Table 4, hereinabove).

Example 6

Adipocyte Differentiation of 2D Adherent Cells 2D adherent cells from bone marrow or placenta origin were stimulated to differentiate into adipocytes.

Materials and Experimental Methods

Adipogenesis

Adipogenesis was carried out according to Chemicon adipogenesis kit (Chemicon adipogenesis kit, cat no. scr020, Millipore, Mass., USA)

Adipogenesis Induction Medium

Adipogenesis induction or maintenance mediums were freshly prepared prior to every medium exchange using the components depicted in Tables 6 and 7, below.

TABLE 6

Adipogenesis induction medium components

| Component | Stock con | Amount | Final con |
|---|---|---|---|
| DMEM low glucose (Biological Industries, Bet Haemek, Israel) | | 4.4 ml | 90% |
| Serum (heat inactivated) | | 0.5 ml | 10% |
| Dexamethasone (Sigma) | 10 mM | 0.5 μl | 1 μM |
| IBMX (Sigma) | 0.5M | 5 μl | 0.5 mM |
| Insulin (Sigma) | 10 mg/ml | 5 μL | 10 μg/ml |
| Indomethacin (Sigma) | 10 mM | 50 μl | 100 μM |
| Pen & Strep | X 100 | 50 μl | X 1 |

TABLE 7

Adipogenesis maintenance medium components

| Component | Stock con | Amount | Final con |
|---|---|---|---|
| DMEM low glucose | | 4.4 ml | 90% |
| Serum (heat inactivated) | | 0.5 ml | 10% |

TABLE 7-continued

Adipogenesis maintenance medium components

| Component | Stock con | Amount | Final con |
|---|---|---|---|
| Insulin | 10 mg/ml | 5 μL | 10 μg/ml |
| Pen & Strep | X 100 | 50 μl | X 1 |

Cell Growth

Placenta derived cells (p1c11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 μg/ml Gentamicin-IKA (Teva Medical) and 0.25 μg/ml Fungizone (Invitrogen, Gibco). Placenta derived cells (4 wells×2 plates) or bone marrow derived cells (1 well×2 plates) were grown until 100% confluent (typically overnight) before initiating adipogenesis differentiation.

When cells reached 100% confluence, growth medium was aspirated and replaced with 1 ml adipogenesis induction medium (differentiation day 1). Adipogenesis induction medium was replaced with fresh medium every 2-3 days for a total of 25 days (as depicted in detail in Table 8, hereinbelow). Of note, monolayers of adipogenic cells were extremely fragile and could easily dislodged from plates, therefore, medium changes were performed with gentle medium changes to avoid disruption of the lipid droplets.

As a control, one of the two plates (for each of the cell types) was not incubated with adipogenesis differentiation medium but rather with the growth medium (described hereinabove).

TABLE 8

Adipogenesis differentiation schedule

| Day | Medium |
|---|---|
| 1 | Adipogenesis Induction medium |
| 3 | Adipogenesis Induction medium |
| 5 | Adipogenesis Induction medium |
| 7 | Adipogenesis Maintenance medium |
| 9 | Adipogenesis Induction medium |
| 11 | Adipogenesis Induction medium |
| 13 | Adipogenesis Induction medium |
| 15 | Adipogenesis Maintenance medium |
| 17 | Adipogenesis Induction medium |
| 19 | Adipogenesis Induction medium |
| 21 | Adipogenesis Induction medium |

On day 25, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 μl) was added to the cells. Cells were incubated with oil red solution at room temperature for 50 minutes. Oil red solution was removed and the cells were washed 4 times with 1 ml water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Experimental Results

Adipocyte differentiation of placenta- or bone marrow-derived adherent cells in adipocyte induction medium resulted in differentiation of over 50% of the bone marrow derived cells (see FIG. 4C), as demonstrated by positive oil red staining and by typical morphological changes (e.g. accumulation of oil droplets in the cytoplasm). In contrast, none of the placental derived cells differentiated into adipocytes (see FIG. 4F and Table 4, hereinabove).

Example 7

Adipocyte Differentiation of 2D Adherent Cells in Modified Growth Medium 2D adherent cells from bone marrow or placenta origin were stimulated to differentiate into adipocytes in a modified medium comprising a higher level of Indomethacine.

Materials and Experimental Methods

Adipogenesis Induction Medium

Adipogenesis induction medium was freshly prepared prior to every medium exchange using the components depicted in Table 9, below.

TABLE 9

Adipogenesis induction medium components

| Component | Stock con | Amount | Final con |
|---|---|---|---|
| DMEM low glucose | | 4.4 ml | 90% |
| Serum (heat inactivated) | | 0.5 ml | 10% |
| Dexamethasone (Sigma) | 1 mM | 5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 200 µl | 100 µM |
| Gentamycine (Biological Industries) | | 10 µl | |

Cell Growth

Placenta derived cells (PLC 8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (5 wells×2 plates).

Bone marrow derived cells (BM109) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 well×2 plates). Cells were grown until 100% confluent (typically overnight) before initiating adipogenesis differentiation.

When cells reached 100% confluence, growth medium was aspirated and replaced with 0.5 ml adipogenesis induction medium (differentiation day 1). Adipogenesis induction medium was replaced with fresh medium every 2-3 days for a total of 3-4 weeks.

As a control, one of the two plates (for each of the cell types) was not incubated with adipogenesis differentiation medium but rather with the growth medium (described hereinabove).

On day 26, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 µl) was added to the cells. Cells were incubated with oil red solution at room temperature for 50 minutes. Oil red solution was removed and the cells were washed 3 times with 1 ml double distilled water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Experimental Results

Adipocyte differentiation of placenta- or bone marrow-derived adherent cells was performed by modification of the protocol in Example 6, hereinabove, according to previous teachings [Parloni et al. (2007), supra]. The main difference between the growth conditions presented in Example 6 and the results presented herein was the higher concentration of Indomethacine. As evident from the results, over 50% of the bone marrow derived cells underwent differentiation into adipocytes (see FIG. 5C), as demonstrated by positive oil red staining and by typical morphological changes (e.g. accumulation of oil droplets in the cytoplasm). In contrast, none of the placental derived cells exhibited morphological changes typical of adipocytes (see FIG. 5F and Table 4, hereinabove).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of culturing undifferentiated adherent cells from a human placenta, the method comprising:
   (i) culturing the undifferentiated adherent cells from the human placenta under 2 dimensional (2D) culturing conditions which allow differentiation-less cell expansion, said conditions comprising passaging of said cells for at least 4 passages and growing the cells in a culture medium devoid of an antibiotic from at least passage 2, wherein the undifferentiated adherent cells have been obtained by enzymatic digestion of said placenta, are heterogeneous with regards to fetal versus maternal origin and are negative for CD11b, CD34, HLA-DR, CD14, CD19, CD200 and CD45; and, (ii) after culturing, freezing the undifferentiated adherent cells in a controlled temperature reducing process, comprising lowering the temperature at a rate of a predetermined number of degrees per minute.

2. The method of claim 1, further comprising obtaining the undifferentiated adherent cells from the human placenta by enzymatically digesting human placental tissue to release said cells, and allowing the released cells to adhere to a culture surface.

3. The method of claim 2, wherein the human placental tissue is enzymatically digested with collagenase.

4. The method of claim 1, wherein the step of freezing the undifferentiated adherent cells is performed at a passage in a range of 6 to 9 passages.

5. The method of claim 1, wherein the step of freezing the undifferentiated adherent cells is performed at a passage in a range of 5 to 8 passages.

6. The method of claim 5, wherein the step of freezing the undifferentiated adherent cells is performed at a passage in a range of 5 to 6 passages.

7. The method of claim 1, wherein the first passage is performed when the cells reach 7 to 15 days in culture.

8. The method of claim 1, wherein, beginning at passage 2, and continuing for 6 to 8 passages, cells are passaged when the culture is at 70% to 90% confluence.

9. The method of claim 1, wherein at each passage the cells are seeded at a density of $4\pm0.5\times10^3$ cells/cm$^2$ of culture surface.

10. The method of claim 1, wherein the step of freezing comprises freezing the undifferentiated adherent cells at a concentration of about $10\times10^6$ cells/ml.

11. The method of claim 1, wherein the adherent cells do not differentiate into osteocytes.

12. The method of claim 1, wherein said adherent stromal cells are positive for a marker selected from the group consisting of CD73, CD90, CD29 and CD105.

13. The method of claim 12, wherein said adherent cells are positive for CD73, CD90, CD29 and CD105.

14. The method of claim 1 further comprising expanding the undifferentiated adherent cells from the human placenta under three-dimensional (3D) culture conditions.

15. The method of claim 14, wherein the 3D culture conditions comprise culturing of the undifferentiated adherent cells on 3D carriers in a bioreactor.

* * * * *